United States Patent
Mount et al.

(10) Patent No.: US 9,560,848 B2
(45) Date of Patent: Feb. 7, 2017

(54) METHOD AND COMPOSITIONS FOR BIOFOULING DETERRENCE

(75) Inventors: Andrew S. Mount, Mountain Rest, SC (US); Neeraj V. Gohad, Clemson, SC (US); Andrew Metters, Clemson, SC (US); Nihar M. Shah, Woodland, CA (US)

(73) Assignee: Clemson University, Clemson, SC (US)

( * ) Notice: Subject to any disclaimer, the term of this patent is extended or adjusted under 35 U.S.C. 154(b) by 1117 days.

(21) Appl. No.: 12/933,476

(22) PCT Filed: Mar. 24, 2009

(86) PCT No.: PCT/US2009/001818
§ 371 (c)(1),
(2), (4) Date: Jan. 26, 2011

(87) PCT Pub. No.: WO2009/134303
PCT Pub. Date: Nov. 5, 2009

(65) Prior Publication Data
US 2011/0123477 A1    May 26, 2011

Related U.S. Application Data

(60) Provisional application No. 61/039,032, filed on Mar. 24, 2008.

(51) Int. Cl.
*A01N 33/10*    (2006.01)
(52) U.S. Cl.
CPC .................................... *A01N 33/10* (2013.01)
(58) Field of Classification Search
None
See application file for complete search history.

(56) References Cited

U.S. PATENT DOCUMENTS

| | | |
|---|---|---|
| 3,575,123 A | 4/1971 | Shepard et al. |
| 2006/0009550 A1 | 1/2006 | Messersmith et al. |
| 2008/0003288 A1 | 1/2008 | Bromberg et al. |
| 2008/0020015 A1 | 1/2008 | Carpenter et al. |
| 2008/0149566 A1* | 6/2008 | Messersmith et al. ....... 210/702 |

FOREIGN PATENT DOCUMENTS

| WO | WO 2006/096129 | 9/2006 |
|---|---|---|
| WO | WO 2008/049108 | 4/2008 |

OTHER PUBLICATIONS

Yamamoto et al., Biofouling: The Journal of Bioadhesion and Biofilm Research 13: 69-82 (1998).*
Siedenbiedel et al., "Antimicrobial Polymers in Solution and on Surfaces: Overview and Functional Principles", Polymers 4: 46-71 (2012).*
PCT International Search Report for PCT/US2009/01818, dated Sep. 29, 2009.
Yamamoto et al; "Neurotransmitter Blockers as Antifoulants Against Planktonic Larvae of the Barnacle *Balanus amphitrite* and the Mussel *Mytilus galloprovincialis*"; Biofouling, vol. 13, Aug. 1, 1998; abstract.
Extended European Search Report for EP09739106, dated Jan. 28, 2013.
Coon et al., "Induction of Settlement and Metamorphosis of the Pacific Oyster, *Crassostrea gigas* (Thunberg), by L-Dopa and Catecholamines" J. Exp. Mar. Biol. Ecol., 1985, vol. 94, pp. 211-221.

* cited by examiner

*Primary Examiner* — Robert A Wax
*Assistant Examiner* — Thor Nielsen
(74) *Attorney, Agent, or Firm* — Dority & Manning, P.A.

(57) ABSTRACT

A method of deterring biofouling of a surface comprising attaching an adduct having formula (I) or noradrenalin to the surface. Formula (I) being defined as compounds that have the formula A-L-R wherein A is i) a C6 or C10 substituted aryl ring, or ii) a C1-C9 substituted or unsubstituted heteroaryl ring: L is a linking group, and R is a primary amino moiety comprising unit.

18 Claims, 10 Drawing Sheets

S3400N 20.0kV 11.6mm    50.0μm
x1.10k SE 9/19/2007

S4800 5.0kV 6.6mm    40.0μm
x1.30k SE(M) 9/28/2007

S4800 5.0kV 6.5mm    20.0μm
x2.50k SE(M) 9/28/2007

S4800 5.0kV 6.6mm    5.00μm
x9.00k SE(M) 9/28/2007

S4800 5.0kV 6.5mm    2.00μm
x20.0k SE(M) 9/28/2007

S3400N 20.0kV 10.9mm    20.0μm
x2.50k SE 9/17/2007

METHOD AND COMPOSITIONS FOR BIOFOULING DETERRENCE

CROSS-REFERENCE TO RELATED APPLICATIONS

This application is the national stage entry of International Patent Application Number PCT/US2009/001818 having International Publication Number WO 2009/134303, which claims the benefit of U.S. Provisional Application No. 61/039,032, filed Mar. 24, 2008, which application is incorporated herein in its entirety by this reference.

STATEMENT OF GOVERNMENT RIGHTS

This invention was made with government support under Grants #N00014-05-1-0468 awarded by United States Office of Naval Research. The government has certain rights in the invention.

BACKGROUND OF THE INVENTION

Field of the Invention

This invention relates generally to fouling deterrence.

Background

Biofouling or biological fouling is the undesirable accumulation of micro-organism, plants, algae, and animals on submerged structures, especially ships' hulls. Biofouling also occurs on the surfaces of living marine organisms, when it is known as epibiosis.

The control of biofouling on artificial surfaces is a significant problem for structures in contact with the marine environment. Historically, anti-biofouling coatings utilized biocides that leach out from the coating over time to thereby prevent biofouling settlement by virtue of the biocides toxicity to marine organisms. This method of control has had a number of problems associated therewith. First, the biofouling resistance of the coating decreases with time as the biocides are depleted by their leaching out. Furthermore, the toxic coatings increase the danger of toxic exposure to shipyard workers, create a hazardous waste disposal problem, and have a detrimental environmental impact on marine wildlife. Subsequent to the removal of environmentally hazardous organo-tin compounds from antifouling paints, control of biofouling accumulation has become the single most expensive maintenance problem incurred by the U.S. Navy for ship operations.

The need for anti-biofouling methods is evident in U.S. Department of the Navy, NAVSEA'S coating needs, which are based on criteria such as environmental drivers (copper-free or low copper (UNDS limits pending)), cost drivers (up front cost and maintenance (313 Ship Navy)) and operational cost (12-year dry docking interval and minimal in-service cleaning).

Along the coasts of the North Atlantic Ocean, barnacles and different kinds of algae are particularly apparent problems. The fully grown barnacle is a stationary crustacean (arthropod), characterized by a centimeter-sized cone shape and enclosing layers of calcinous plates. The mechanical strength of the animal's attachment to solid surfaces is very high, and it is therefore difficult to mechanically remove barnacles from solid surfaces. The animal undergoes different development stages as free-swimming larvae, where the last larva stage is referred to as the cyprid stage. The cyprid screens solid surfaces suitable for settling with the help of a nervous protuberance, the antennule. A "settling-glue" referred to as balanus cement is secreted from specialized glands localized near the protuberance and the animal thereby settles to the solid surface. After settlement the animal undergoes a metamorphosis into an adult and stationary animal.

The common name oyster is used for a number of different groups of bivalve mollusks, most of which live in marine habitats or brackish water. The shell consists of two usually highly calcified valves which surround a soft body. Gills filter plankton from the water, and strong adductor muscles are used to hold the shell closed. Oysters are a biofouling species. The pediveliger larva is last larval stage of an oyster in which the veliger larva (characterized by a ciliated lobe (or lobes) known as the velum which functions in propulsion and food-gathering) develops a foot and seeks a substrate on which to settle. The settling and cementation process leads to biofouling of the substrate.

SUMMARY OF THE INVENTION

Provided are compositions and methods to deter biofouling.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate (one) several embodiment(s) of the invention and together with the description, serve to explain the principles of the invention.

DETAILED DESCRIPTION

Figure 1:
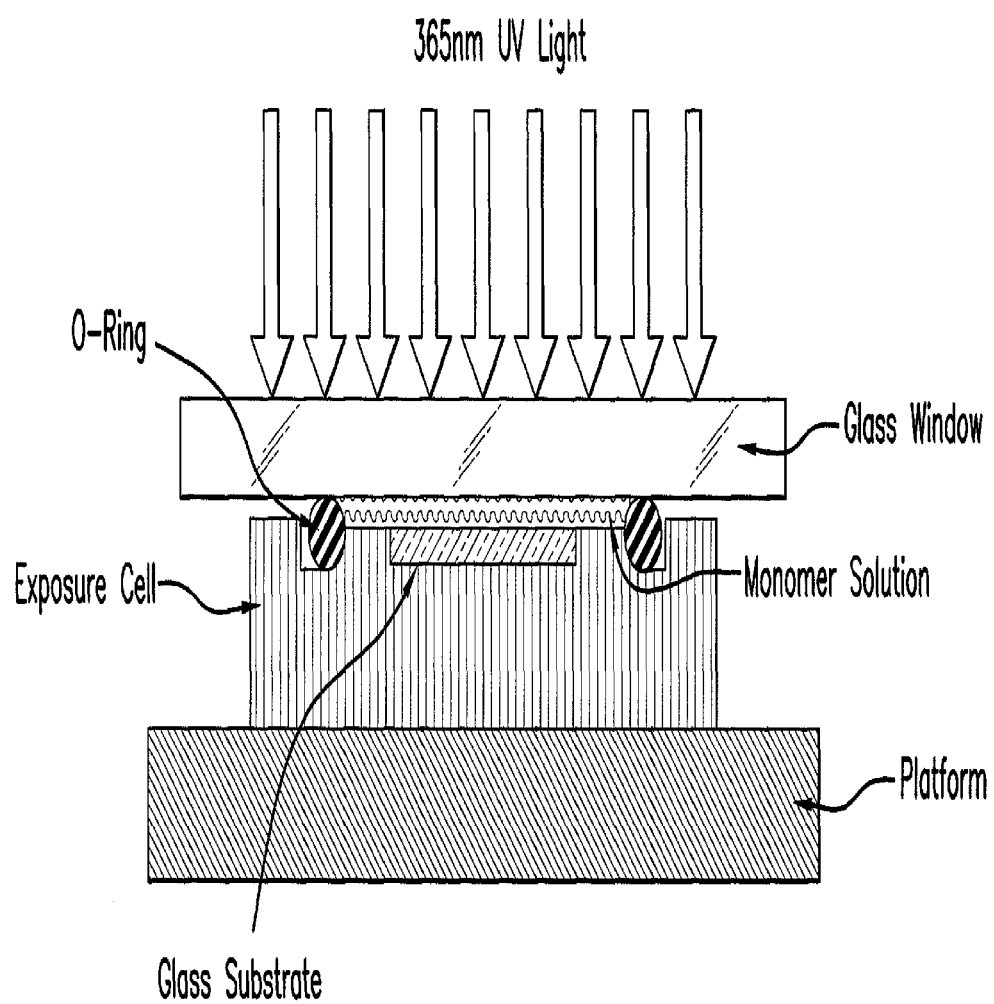
FIG. 1 shows the mask aligner system used to graft polymer from glass substrates using 365 nm UV light at constant 25 mW/cm$^2$ intensity. This figure shows the assembly for only one of the samples.

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods, specific signaling molecules, specific biofouling organisms, or to particular surfaces, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "an aromatic compound" includes mixtures of aromatic compounds, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings: "Optional" or "optionally" means that the subsequently described event or circumstance may or may not occur, and that the description includes instances where said event or circumstance occurs and instances where it does not.

Reference will now be made in detail to the present preferred embodiment(s) of the invention, an example(s) of which are illustrated in the accompanying drawings.

Provided are compounds, compositions and methods of using said compositions that prevent the adhesion of organisms to surfaces. Such compounds include the compound of formula I, noradrenaline (NA), biomimetics of the compound of formula I and biomimetics of NA.

A composition comprising a noradrenalin linked to a polymer is provided. In this composition, the polymer can be methacrylic acid. In this composition, the polymer can be 2-hydroxyethyl methacrylate.

A non-toxic coating composition is provided, comprising (i) an adduct having formula I; and (ii) a film forming agent, said noradrenalin being present in said composition in an amount effective to inhibit the attachment of biofouling organisms on a surface to which said composition is applied. In this composition, the adduct having formula I can be present in an amount from about 30 µM to about 100 µM. In the composition, the adduct having formula I can be covalently attached to the film forming agent.

A paint comprising the non-toxic coating composition disclosed herein is provided. This paint can be formulated as a marine paint. A varnish comprising the non-toxic coating composition is also provided.

An anti-fouling surface comprising an effective amount of an adduct having Formula I, wherein the compound or a biologically active fragment thereof is released from the surface.

Surfaces in contact with marine environments (which include fresh water, brackish water and salt water environments) are known to become fouled by various types of microorganisms and macro organisms. Vulnerable surfaces include, for example, the hulls of ships, surfaces of docks, the inside of pipes in circulating or pass-through water systems, aqua culture equipment and oil/gas off-shore installations, pipelines (water pipes and sewer pipes), power plant water intake systems, heat exchangers, grids, fish nets, cages, etc. Attaching themselves to these surfaces, organisms not only impede water flow across the surface hampering performance, but can also cause deterioration of the surface itself.

Many other surfaces are susceptible to similar biofouling, for example walls exposed to rain water, walls of showers, roofs, gutters, pool areas, saunas, floors and walls exposed to damp environs such as basements or garages and even the housing of tools and outdoor furniture.

It is highly undesirable for organisms to become established or to spread on any of these surfaces. Slime layers frequently form, and these can lead to unsafe, unhealthy or unaesthetic conditions.

The compositions and methods of this invention are readily applied to a variety of surfaces and, without limiting the method and compositions, appear to function more by preventing adhesion (settling and cementation) of an organism to a surface rather than by acute toxic activity rendering said compositions more environmentally acceptable.

Methods

A method of deterring biofouling of a surface comprising attaching an adduct having Formula I to the surface is provided. An example of an adduct of Formula I is noradrenalin. Thus, provided is a method of deterring biofouling of a surface comprising attaching noradrenalin to the surface.

Also provided is a method of deterring biofouling of a surface, comprising attaching a mimetic of formula I to the surface. The formula I mimetic is provided based on known structure-based drug design methods described herein. Also provided is a method of deterring biofouling of a surface, comprising attaching a noradrenaline biomimetic to the surface. The NA biomimetic is provided based on known structure-based drug design methods described herein.

Thus, provided is a method of deterring biofouling of a surface comprising attaching a compound that is a biomimetic of formula I to the surface. More specifically, provided is a method of deterring biofouling of a surface comprising attaching a compound that is a biomimetic of NA to the surface.

A further method of deterring biofouling of a surface comprising attaching an agonist for a G-protein coupled receptor (GPCR) to the surface is provided. For example, a method of deterring biofouling of a surface comprising attaching an agonist of a β-adrenergic receptor to the surface is provided. In the disclosed method of deterring biofouling of a surface, the agonist of a β-adrenergic receptor can be noradrenalin.

Provided is a method of preventing marine biofouling of a substrate by a marine biofouling organism, comprising applying a protective coating to the substrate, said coating containing noradrenalin bound to a polymer backbone selected from the group consisting of monomers methacrylic acid (MAA; 99%, Aldrich) and 2-hydroxyethyl methacrylate (HEMA; ≥99%, Sigma).

In the disclosed method, the signaling molecule for a GPCR is attached to the surface using a monomer that has reactive side groups to which the signaling molecule can bind. For example a monomer with —COOH or —OH as reactive side groups is particularly useful. For example, the signaling molecule can be attached to the surface by a monomer selected from the group consisting of methacrylic acid and 2-hydroxyethyl methacrylate. Thus provided is a method of deterring biofouling, wherein noradrenalin is attached to the surface by a monomer selected from the group consisting of methacrylic acid and 2-hydroxyethyl methacrylate.

Where monomers are used, they are polymerized to present very high surface concentration of reactive side groups, compared to using just a single molecular layer. The method and compositions can use a single layer of —OH groups to attach the signaling molecule to the surface, but the concentration of signaling molecule in this system is expected to be lower than with polymerized monomer, and may exhibit a reduction in the biological effects seen using the disclosed bioactive polymer surfaces. The two key requirements of attaching the signaling molecule (e.g. NA) to a surface are the bond strength and accessibility. By using surface grafted polymer chains to attach the signaling molecule, the mobility and the accessibility of signaling molecule is retained in spite of molecule being covalently attached to the surface. This prevents the signaling molecule from being washed away during exposure to a liquid environment or from being removed by the cells themselves.

In the method of deterring biofouling, the surface can be a surface exposed to a marine environment. Examples of surfaces that are exposed a marine environment for which the present method is effective to deter biofouling include surfaces selected from the group consisting of the hull of a ship, a propeller, a seismic streamer, a dock, an oil rig, a gas rig, a pipeline, a power plant water intake system, a heat exchanger, a grids, a fish net, a cage. Since the present method is based molecular signaling the method can be used on any substrate to which the signaling molecule can be attached. It is recognized that surfaces comprised of many different materials, e.g., metal, wood, concrete, tissue, plastic, etc., benefit from the present method of attaching a GPCR signaling molecule (e.g., an agonist such as NA) to the surface. The relevant consideration is the ability to attach a sufficient concentration of signaling molecule to the surface. The examples teach how practice the attachment chemistry and identify sufficient concentrations of signaling molecule.

The present methods and compositions are can deter biofouling by mollusks. A method of deterring biofouling of a surface by mollusks comprising attaching a signaling molecule for a G-protein coupled receptor (GPCR) to the surface is provided. For example, a method of deterring biofouling of a surface by a mollusk comprising attaching an agonist of a adrenergic receptor to the surface is provided. In a method of deterring biofouling of a surface by a mollusk comprising attaching an agonist of a β-adrenergic receptor to the surface, the agonist of a β-adrenergic receptor can be noradrenalin. In the method of preventing biofouling by a mollusk, the mollusk is selected from the group consisting of oysters. In the disclosed methods of preventing biofouling, the biofouling mollusk can be Pectimidae (*Placopecten magellanicus*) or Mytilidae (*Mytilus edulis*). Thus, in a specific example, provided is a method of preventing the settling of and cementation of a mollusk on a surface, comprising attaching noradrenalin to the surface. In a more specific example, provided is a method of preventing the settling of and cementation of an oyster larva on a surface, comprising attaching the compound of formula I (e.g., noradrenalin) to the surface. In a more specific example, provided is a method of preventing the settling of and cementation of a Pectimidae larva on a surface, comprising attaching the compound of formula I (e.g., noradrenalin) to the surface. In a further specific example, provided is a method of preventing the settling of and cementation of a Mytilidae larva on a surface, comprising attaching the compound of formula I (e.g., noradrenalin) to the surface.

The disclosed biofouling deterrence methods and compositions have particular applicability in oyster culture. A significant problem in oyster culture is the settlement and attachment of oyster larvae on the shells of other oysters. This clumping affects the shape of the oyster shell in a way that makes it less commercially valuable. Because the present method prevents settling and cementation of oyster larvae on the shells of mature oysters, greater numbers of commercially preferred oysters can be grown and harvested.

The present methods and compositions are can deter biofouling by crustaceans. A method of deterring biofouling of a surface by crustaceans comprising attaching a signaling molecule for a G-protein coupled receptor (GPCR) to the surface is provided. For example, a method of deterring biofouling of a surface by a crustacean comprising attaching an agonist of a β-adrenergic receptor to the surface is provided. In a method of deterring biofouling of a surface by a crustacean comprising attaching an agonist of a β-adrenergic receptor to the surface, the agonist of a β-adrenergic receptor can be noradrenalin. In the method of preventing biofouling by a crustacean, the crustacean is selected from the group consisting of barnacles. Thus, in a specific example, provided is a method of preventing the settling of and cementation of a crustacean on a surface, comprising attaching noradrenalin to the surface. In a more specific example, provided is a method of preventing the settling of and cementation of a barnacle cyprid on a surface, comprising attaching noradrenalin to the surface.

The present methods and compositions are can deter biofouling by other marine invertebrate species.

The present methods and compositions are can deter biofouling by members of the phylum Bryozoa. A method of deterring biofouling of a surface by a Bryozoan comprising attaching a signaling molecule for a G-protein coupled receptor (GPCR) to the surface is provided. For example, a method of deterring biofouling of a surface by a Bryozoan comprising attaching an agonist of a β-adrenergic receptor to the surface is provided. In a method of deterring biofouling of a surface by a Bryozoan comprising attaching an agonist of a β-adrenergic receptor to the surface, the agonist of a β-adrenergic receptor can be noradrenalin. In the method of preventing biofouling by a Bryozoan, the Bryozoan is selected from the group consisting of *Bugula neritina*. Thus, in a specific example, provided is a method of preventing the settling of and cementation of a Bryozoan larva on a surface, comprising attaching noradrenalin to the surface. In a more specific example, provided is a method of preventing the settling of and cementation of a *B. neritina* larva on a surface, comprising attaching noradrenalin to the surface.

The present methods and compositions can deter biofouling by polychaetes. A method of deterring biofouling of a surface by a polychaet comprising attaching a signaling molecule for a G-protein coupled receptor (GPCR) to the surface is provided. For example, a method of deterring biofouling of a surface by a polychaet comprising attaching an agonist of a β-adrenergic receptor to the surface is provided. In a method of deterring biofouling of a surface by a polychaet comprising attaching an agonist of a β-adrenergic receptor to the surface, the agonist of a β-adrenergic receptor can be noradrenalin. In the method of preventing biofouling by a polychaet, the polychaet is selected from the group consisting of *Hydroides elegans*. Thus, in a specific example, provided is a method of preventing the settling of and cementation of a polychaet larva on a surface, comprising attaching noradrenalin to the surface. In a more specific example, provided is a method of preventing the settling of and cementation of a *H. elegans* larva on a surface, comprising attaching noradrenalin to the surface.

A non-toxic biofouling deterrence system is provided, comprising: a polymer-based coating disposed on a submarine surface, wherein the coating comprises the adduct of Formula I. A further example of the non-toxic biofouling deterrence system is provided, comprising: a polymer-based coating disposed on a submarine surface, wherein the coating comprises a signaling molecule for a GPCR. In a specific example of the non-toxic biofouling deterrence system, the coating comprises noradrenalin. The amount of NA in the coating is an amount sufficient to reduce larval settling and/or cementation to the coated surface.

The present methods deter biofouling longer than other antifouling methods and compositions.

Drug Design

The disclosed compositions, e.g., NA can be used as targets for any molecular modeling technique to identify either the structure of the disclosed compositions or to identify potential or actual molecules, such as small molecules, which interact in a desired way with the receptor for NA. The compound of formula I and related molecules disclosed herein can be used as targets in any molecular modeling program or approach.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as, formula I and NA, are also disclosed. Thus, the products produced using the molecular modeling approaches that involve the disclosed compositions, such as, Formula I and NA, are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 19891 J. Am. Chem. Soc. 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

A specific example of an approach to affect biomimetic NA design is as follows: (1) maintaining the shape and size dimensions of the NA ring structure but modify the hydroxyl groupings (—OH); and (2) produce a linear carbon chain that would look like HO—C—C—C(NH3)-C≡C—OH. The NH3 group on the middle carbon would be covalently linked to the polymer backbone (surface).

In a further approach to provide a biomimetic of NA, a seminal paper on structure based receptor design (I. Kuntz, Structure-Based Strategies for Drug Design and Discovery, Science, Vol. 257: 1078-1082, 1992), which describes the process for designing a compound based on the structure of a receptor. This reference is incorporated herein by reference for its teaching of the process of designing a drug based on the structure of a receptor. For example the compound designed can be a mimetic of a ligand for a receptor As a further example, the x-ray crystallographic structure of NA within the cleft of the NA receptor can be used to design a mimetic for NA. For example Rasmussen et al. (Nature, Vol. 450; 338-388, 15 Nov. 2007) provide the crystallographic structure of the human $\beta_2$ adrenoceptor ($\beta_2AR$), a receptor for NA. This reference is incorporated herein by reference for its teaching of the structure of the binding site of this receptor. Jaakola et al. (*Science*. 2008 Nov. 21; 322(5905):1211-7. Epub 2008 Oct. 2) describe techniques for obtaining the crystal structure of a receptor with a ligand in the binding site. This reference is incorporated herein by reference for its teaching of how to obtain the crystal structure of a receptor binding site. Based on the detailed information about the structure of the receptor and its binding site for NA provided, one of skill can design a compound that will bind in the binding site and mimic the signal of NA. Such a compound can be used in the method of deterring biofouling.

Thus, provided is a method of deterring biofouling of a surface comprising attaching a compound that is a biomimetic of NA to the surface.

Although described above with reference to design and generation of compounds which could inhibit larval settling behavior, one could also screen libraries of known compounds, including natural products or synthetic chemicals, and biologically active materials, including proteins, for compounds which alter settling behavior.

Chemistry of Attachment

The chemistry for attachment of the adduct of Formula I to a surface described herein can be used on an industrial scale. Furthermore, the chemistry for attachment of a GPCR signaling molecule to a surface described herein can be used on an industrial scale. In fact, the photopolymerization techniques for coatings are already used by surface modification industries and is well-known in the literature (de Boer et al. (2000); Harris, B. P. and A. T. Metters (2006)). The conjugation chemistry to attach the NA is very well known and is used by many pharmaceutical companies in commercial drug synthesis. Other methods for attaching a GPCR signaling molecule to a surface can be used in the present method.

In a specific example of the attachment chemistry, the noradrenalin can be bound to a polymer backbone selected from the group consisting of monomers methacrylic acid (MAA; 99%, Aldrich) and 2-hydroxyethyl methacrylate (HEMA; ≥99%, Sigma).

In the disclosed method and composition, the adduct of Formula I is attached to the surface using a monomer that has reactive side groups to which the signaling molecule can bind. In the disclosed method, the signaling molecule for a GPCR is attached to the surface using a monomer that has reactive side groups to which the signaling molecule can bind. For example a monomer with —COOH or —OH as reactive side groups is particularly useful. For example, the signaling molecule can be attached to the surface by a monomer selected from the group consisting of methacrylic acid and 2-hydroxyethyl methacrylate. Thus provided is a method of deterring biofouling, wherein noradrenalin is attached to the surface by a monomer selected from the group consisting of methacrylic acid and 2-hydroxyethyl methacrylate.

Where monomers are used, they are polymerized to present very high surface concentration of reactive side groups, compared to using just a single molecular layer. The method and compositions can use a single layer of —OH groups to attach the signaling molecule to the surface, but the concentration of signaling molecule in this system is expected to be lower than with polymerized monomer, and may exhibit a reduction in the biological effects seen using the disclosed bioactive polymer surfaces. The two key requirements of attaching the signaling molecule (e.g. NA) to a surface are the bond strength and accessibility. By using surface grafted polymer chains to attach the signaling molecule, the mobility and the accessibility of signaling molecule is retained in spite of molecule being covalently attached to the surface.

Compositions

Disclosed herein are bioactive adducts suitable for attachment to the disclosed polymers wherein the bioactive adduct acts as a deterrent to biofouling by oysters (mollusks) and barnacles (crustaceans). The disclosed bioactive adducts therefore proved inhibition of biofouling to surfaces. The compounds have the formula:

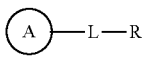

FORMULA I wherein A is:
  i) a $C_6$ or $C_{10}$ substituted aryl ring; or
  ii) a $C_1$-$C_9$ substituted or unsubstituted heteroaryl ring;
L is a linking group; and
R is a primary amino moiety comprising unit.

A Units

A units are aryl or heteroaryl rings substituted by one or more organic moieties disclosed herein. A first category of A units relates to substituted phenyl rings having the formula:

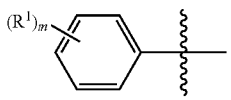

wherein $R^1$ represents from 1 to 5 substitutions for hydrogen on the phenyl ring, the index m is an integer from 1 to 5.

One embodiment relates to A units having 1 or 2 ring substitutions that are hydroxyl groups. Examples of A units according to this embodiment include 2-hydroxyphenyl, 3-hydroxyphenyl, 4-hydroxyphenyl, 2,3-dihydroxyphenyl, 2,4-dihydroxyphenyl, 2,5-dihydroxyphenyl, 2,6-dihydroxyphenyl, 3,4-dihydroxyphenyl, and 3,5-dihydroxyphenyl.

Another embodiment relates to A units having 1 or 2 ring substitutions that are amino groups. Examples of A units according to this embodiment include 2-aminophenyl, 3-aminophenyl, 4-aminophenyl, 2,3-diaminophenyl, 2,4-diaminophenyl, 2,5-diaminophenyl, 2,6-diaminophenyl, 3,4-diaminophenyl, and 3,5-diaminophenyl.

A further embodiment relates to A units having 1 or 2 ring substitutions that are thiol groups. Examples of A units according to this embodiment include 2-thiophenyl, 3-thiophenyl, 4-thiophenyl, 2,3-dithiophenyl, 2,4-dithiophenyl, 2,5-dithiophenyl, 2,6-dithiophenyl, 3,4-dithiophenyl, and 3,5-dithiophenyl.

A yet further embodiment relates to A units having 1 or 2 ring substitutions that are a mixture of hydroxyl and alkoxy groups. Examples of A units according to this embodiment include 2-hydroxy-3-methoxyphenyl, 2-methoxy-3-hydroxyphenyl, 2-methoxy-4-hydroxyphenyl, 2-hydroxy-4-methoxyphenyl, 2-hydroxy-5-methoxyphenyl, 2-hydroxy-6-methoxyphenyl, 3-methoxy-4-hydroxyphenyl, and 3-hydroxy-4-methoxyphenyl.

A still further embodiment relates to A units having 1 or 2 ring substitutions that are a mixture of hydroxyl and alkyl groups. Examples of A units according to this embodiment include 2-hydroxy-3-methylphenyl, 2-methyl-3-hydroxyphenyl, 2-methyl-4-hydroxyphenyl, 2-hydroxy-4-methylphenyl, 2-hydroxy-5-methylphenyl, 2-hydroxy-6-methylphenyl, 3-methyl-4-hydroxyphenyl, and 3-hydroxy-4-methylphenyl.

A still yet further embodiment relates to A units having 1 or 2 ring substitutions that are a mixture of hydroxyl and amino groups. Examples of A units according to this embodiment include 2-hydroxy-3-aminophenyl, 2-amino-3-hydroxyphenyl, 2-amino-4-hydroxyphenyl, 2-hydroxy-4-aminophenyl, 2-hydroxy-5-aminophenyl, 2-hydroxy-6-aminophenyl, 3-amino-4-hydroxyphenyl, and 3-hydroxy-4-aminophenyl.

Another still yet further embodiment relates to A units having 1 or 2 ring substitutions that are a mixture of thiol and amino groups. Examples of A units according to this embodiment include 2-thio-3-aminophenyl, 2-amino-3-thiophenyl, 2-amino-4-thiophenyl, 2-thio-4-aminophenyl, 2-thio-5-aminophenyl, 2-thio-6-aminophenyl, 3-amino-4-thiophenyl, and 3-thio-4-aminophenyl.

Another category of A units relates to substituted phenyl rings having the formula:

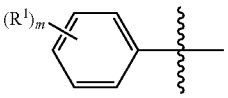

wherein $R^1$ represents from 1 to 5 substitutions for hydrogen on the phenyl ring wherein at least one substitution is a halogen.

One embodiment of this category relates to A units having 1 or 2 ring substitutions that are halogen atoms. Examples of A units according to this embodiment include 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, and 3,5-dichlorophenyl.

Another embodiment of this category relates to A units having 1 or 2 ring substitutions that are halogen atoms and hydroxyl groups. Examples of A units according to this embodiment include 2-hydroxy-3-fluorophenyl, 2-fluoro-3-hydroxyphenyl, 2-fluoro-4-hydroxyphenyl, 2-hydroxy-4-fluorophenyl, 2-hydroxy-5-fluorophenyl, 2-hydroxy-6-fluorophenyl, 3-fluoro-4-hydroxyphenyl, 3-hydroxy-4-fluorophenyl, 2-hydroxy-3-chlorophenyl, 2-chloro-3-hydroxyphenyl, 2-chloro-4-hydroxyphenyl, 2-hydroxy-4-chlorophenyl, 2-hydroxy-5-chlorophenyl, 2-hydroxy-6-chlorophenyl, 3-chloro-4-hydroxyphenyl, and 3-hydroxy-4-chlorophenyl.

Another embodiment of this category relates to A units having 1 or 2 ring substitutions that are halogen atoms and amino groups. Examples of A units according to this embodiment include 2-amino-3-fluorophenyl, 2-fluoro-3-aminophenyl, 2-fluoro-4-aminophenyl, 2-amino-4-fluorophenyl, 2-amino-5-fluorophenyl, 2-amino-6-fluorophenyl, 3-fluoro-4-aminophenyl, 3-amino-4-fluorophenyl, 2-amino-3-chlorophenyl, 2-chloro-3-aminophenyl, 2-chloro-4-aminophenyl, 2-amino-4-chlorophenyl, 2-amino-5-chlorophenyl, 2-amino-6-chlorophenyl, 3-chloro-4-aminophenyl, and 3-amino-4-chlorophenyl.

A further embodiment of this category relates to A units having 1 or 2 ring substitutions that are halogen atoms and thiol groups. Examples of A units according to this embodiment include 2-thio-3-fluorophenyl, 2-fluoro-3-thiophenyl, 2-fluoro-4-thiophenyl, 2-thio-4-fluorophenyl, 2-thio-5-fluorophenyl, 2-thio-6-fluorophenyl, 3-fluoro-4-thiophenyl, 3-thio-4-fluorophenyl, 2-thio-3-chlorophenyl, 2-chloro-3-thiophenyl, 2-chloro-4-thiophenyl, 2-thio-4-chlorophenyl, 2-thio-5-chlorophenyl, 2-thio-6-chlorophenyl, 3-chloro-4-thiophenyl, and 3-thio-4-chlorophenyl.

A yet further embodiment of this category relates to A units having 1 or 2 ring substitutions that are halogen atoms and methyl groups. Examples of A units according to this embodiment include 2-methyl-3-fluorophenyl, 2-fluoro-3-methylphenyl, 2-fluoro-4-methylphenyl, 2-methyl-4-fluorophenyl, 2-methyl-5-fluorophenyl, 2-methyl-6-fluorophenyl, 3-fluoro-4-methylphenyl, 3-methyl-4-fluorophenyl, 2-methyl-3-chlorophenyl, 2-chloro-3-methylphenyl, 2-chloro-4-methylphenyl, 2-methyl-4-chlorophenyl, 2-methyl-5-chlorophenyl, 2-methyl-6-chlorophenyl, 3-chloro-4-methylphenyl, and 3-methyl-4-chlorophenyl.

A still further embodiment of this category relates to A units having 1 or 2 ring substitutions that are halogen atoms and methoxy groups. Examples of A units according to this embodiment include 2-methoxy-3-fluorophenyl, 2-fluoro-3-methoxyphenyl, 2-fluoro-4-methoxyphenyl, 2-methoxy-4-fluorophenyl, 2-methoxy-5-fluorophenyl, 2-methoxy-6-fluorophenyl, 3-fluoro-4-methoxyphenyl, 3-methoxy-4-fluorophenyl, 2-methoxy-3-chlorophenyl, 2-chloro-3-methoxyphenyl, 2-chloro-4-methoxyphenyl, 2-methoxy-4-chlorophenyl, 2-methoxy-5-chlorophenyl, 2-methoxy-6-chlorophenyl, 3-chloro-4-methoxyphenyl, and 3-methoxy-4-chlorophenyl.

Another category of A units relates to substituted or unsubstituted $C_1$-$C_9$ heteroaryl units. One embodiment of heteroaryl A units relates to compounds wherein A is a substituted or unsubstituted $C_2$, $C_3$, or $C_4$ heteroaryl or heterocyclic 5-member ring chosen from:

i) a pyrrolidinyl ring having the formula;

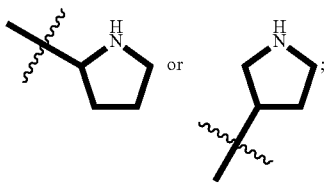

ii) a pyrrolyl ring having the formula:

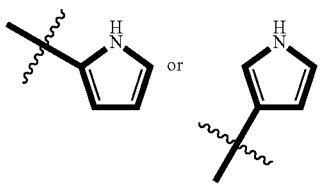

iii) a 4,5-dihydroimidazolyl ring having the formula:

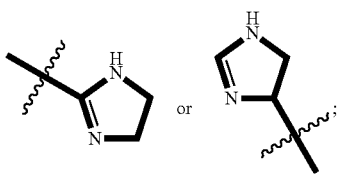

iv) a pyrazolyl ring having the formula:

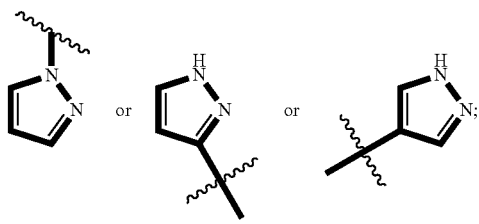

v) an imidazolyl ring having the formula:

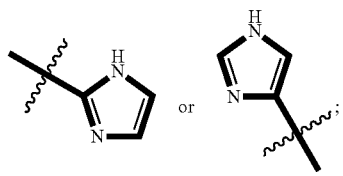

vi) a [1,2,3]triazolyl ring having the formula:

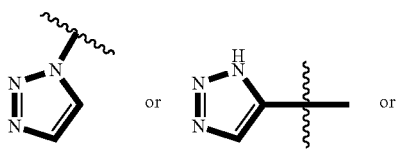

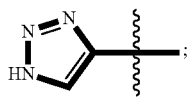

vii) a [1,2,4]triazolyl ring having the formula:

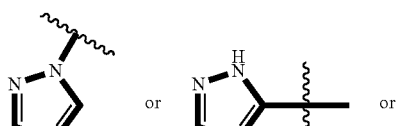

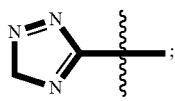

viii) tetrazolyl ring having the formula:

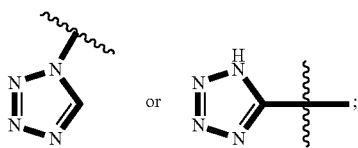

ix) a [1,3,4] or [1,2,4]oxadiazolyl ring having the formula:

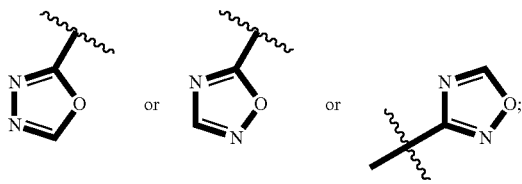

x) a pyrrolidinonyl ring having the formula:

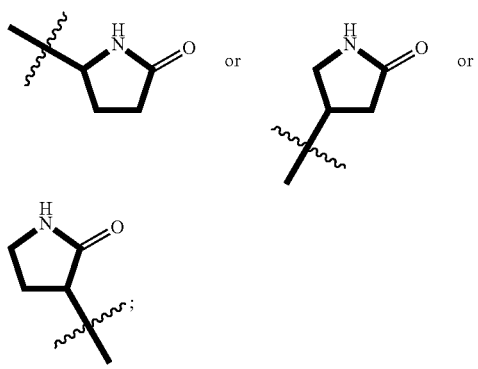

xi) an imidazolidinonyl ring having the formula:

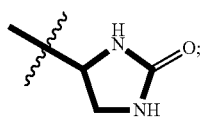

xii) an imidazol-2-only ring having the formula:

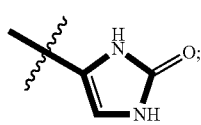

xiii) an oxazolyl ring having the formula:

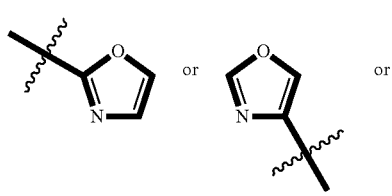

xiv) an isoxazolyl ring having the formula:

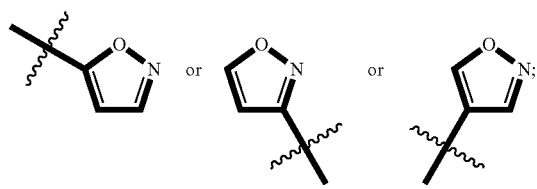

xv) a dihydrothiazolyl ring having the formula:

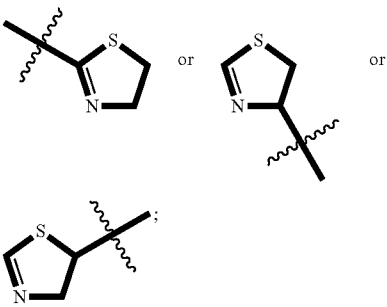

xvi) a furanly ring having the formula:

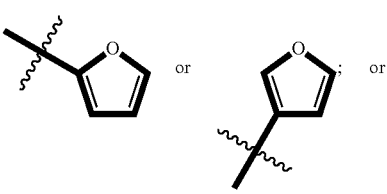

xvii) a thiophenyl having the formula:

Non-limiting examples of units which are suitable for substitution of one or more hydrogen ring atoms of the $C_2$, $C_3$, or $C_4$ heteroaryl or heterocyclic 5-member ring are independently chosen from;
i) hydroxyl;
ii) amino;
iii) thiol;
iv) phenyl;
v) $C_1$-$C_4$ linear or branched alkyl; or
vi) $C_1$-$C_4$ linear or branched alkoxy.

Non-limiting examples of substituted $C_2$, $C_3$, or $C_4$ heteroaryl or heterocyclic 5-member rings include:

i) 3-methylisoxazol-5-yl and 5-methylisoxazol-3-yl having the formulae:

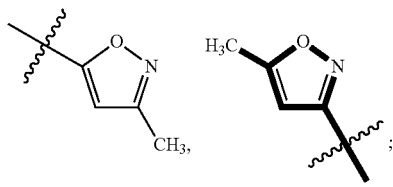

ii) 3-methyl-5-phenylisoxazol-4-yl and 3-phenyl-5-methylisoxazol-4-yl having the formulae:

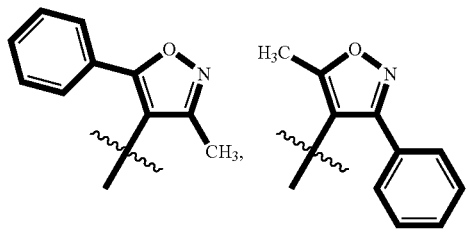

iii) 3,5-dimethylpyrazol-1-yl having the formulae:

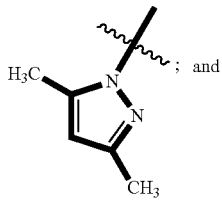

iv) 2-methlpyrrol-1-yl and 3-methylpyrrol-1-yl having the formulae;

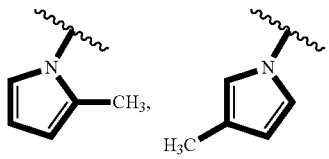

Another embodiment of this category of A units relates to substituted or unsubstituted $C_3$, $C_4$ or $C_5$ heteroaryl 6-member rings, non-limiting examples of which are chosen from:

i) a pyridinyl ring having the formula:

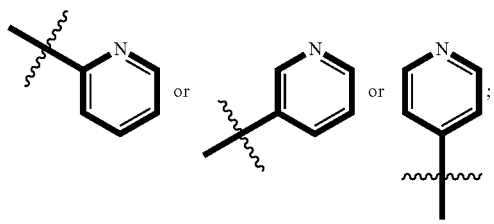

ii) a pyrimidinyl ring having the formula:

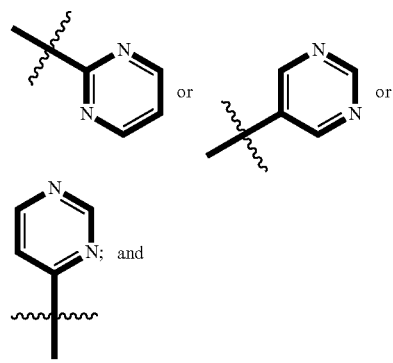

iii) a triazinyl ring having the formula:

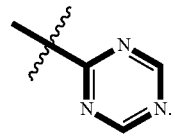

Non-limiting examples of units which are suitable for substitution of one or more hydrogen ring atoms of the $C_2$, $C_3$, or $C_4$ heteroaryl 6-member ring are independently chosen from:

i) hydroxyl;
ii) amino;
iii) thiol;
iv) phenyl;
v) $C_1$-$C_4$ linear or branched alkyl; or
vi) $C_1$-$C_4$ linear or branched alkoxy.

Non-limiting examples of substituted $C_3$, $C_4$, or $C_5$ heteroaryl or heterocyclic 6-member rings include:

4,6-dimethylpyrimidin-2-yl and 4-hydroxy-6-methylpyrimidin-2-yl having the formulae;

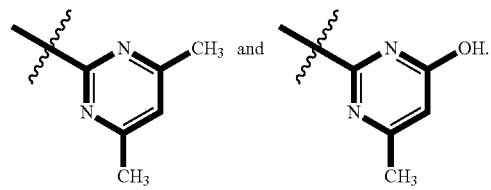

A further embodiment of this category of A units relates to substituted or unsubstituted $C_7$, $C_8$ or $C_9$ heteroaryl fused rings, non-limiting examples of which are chosen from:

i) benzoimidazolyl rings having the formula:

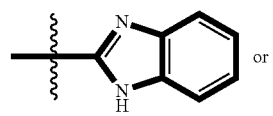

-continued

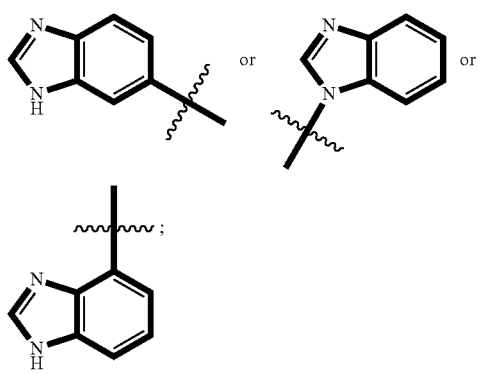

ii) benzothiazolyl rings having the formula:

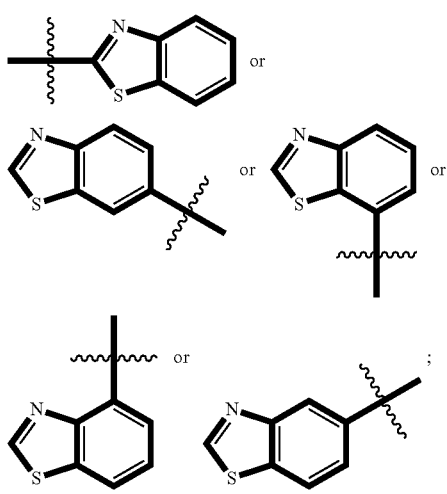

iii) benzoxazolyl rings having the formula:

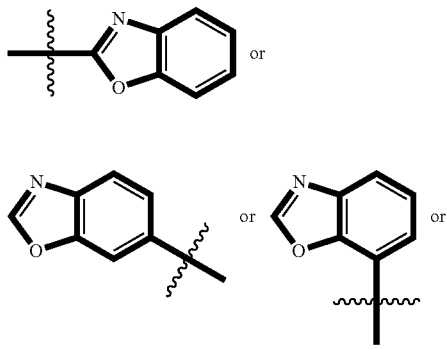

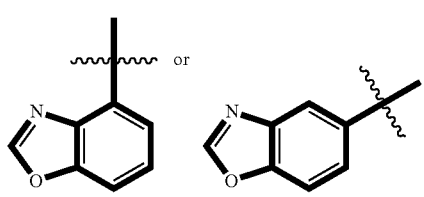

iv) quinazolinyl rings having the formula:

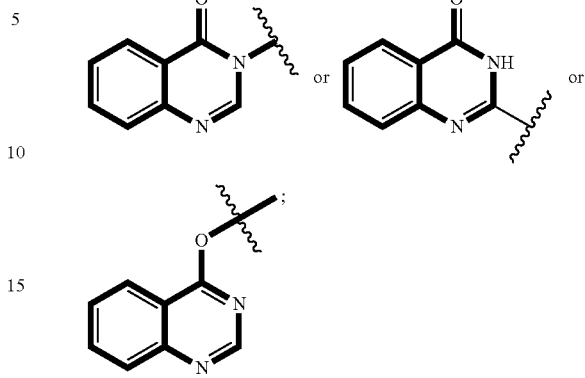

v) 2,3-dihydrobenzo[1,4]dioxinyl rings having the formula:

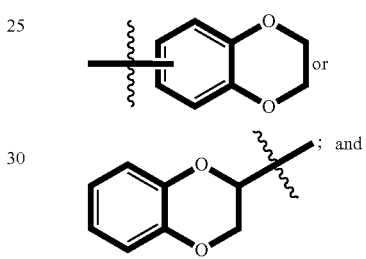

vi) tetrahydroquinolinyl rings having the formula:

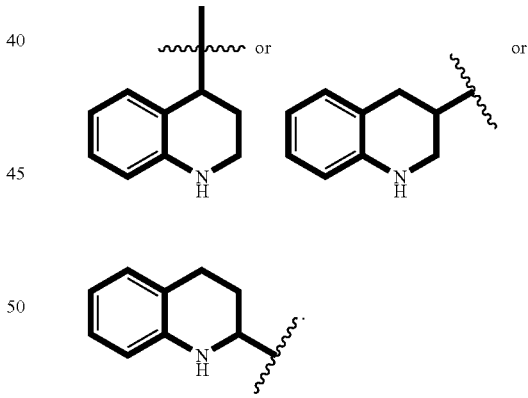

Non-limiting examples of units which are suitable for substitution of one or more hydrogen ring atoms of the $C_7$, $C_8$, or $C_9$ heteroaryl or heterocyclic fused rings are independently chosen from:

i) hydroxyl;
ii) amino;
iii) thiol;
iv) phenyl;
v) $C_1$-$C_4$ linear or branched alkyl; or
vi) $C_1$-$C_4$ linear or branched alkoxy.

Non-limiting examples of substituted $C_7$, $C_8$, or $C_9$ heteroaryl or heterocyclic fused rings include:

2-methylquinazolin-4-yl and 2-methylquinazolinon-3-yl having the formulae:

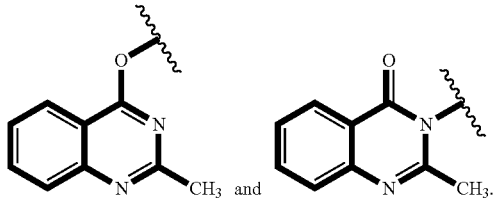

R Units

R units are primary amino moiety comprising units, as such any organic unit comprising a —$NH_2$ amino moiety, including —$NH_2$ alone is suitable as an R unit.

L Units

L units are linking units that connect the R units and the A units. However, L units can comprise an amino moiety in addition to the amino moiety that comprises the R unit.

Linking units L, $L^1$, $L^2$, $L^3$, and $L^4$ are each independently chosen from:
i) —$(CR^{2a}R^{2b})_x$—; or
ii) —$(CR^{3a}R^{3b})_w[O(CR^{4a}R^{4b})_y]_z$—;
wherein $R^{2a}$, $R^{2b}$, $R^{3a}$, $R^{3b}$, $R^{4a}$, and $R^{4b}$ are each independently chosen from:
i) —H;
ii) —$(CR^{5a}R^{5b})_p$OH;
iii) —$(CR^{5a}R^{5b})_p$$NH_2$; and
iv) —$(CR^{5a}R^{5b})_p$$CH_3$;
wherein $R^{5a}$, and $R^{5b}$ are each independently hydrogen or methyl; the index p is an integer from 0 to 5; the index w is an integer from 2 to 6; the index x is an integer from 1 to 10; the index y is an integer from 2 to 6; and the index z is an integer from 1 to 5.

A first category of L linking units relates to alkylene units having the formula:

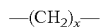

wherein $R^{2a}$ and $R^{2b}$ are each hydrogen; and the index m is from 1 to 10. Non-limiting examples of this category include:
i) —$CH_2$—;
ii) —$CH_2CH_2$—;
iii) —$CH_2CH_2CH_2$—;
iv) —$CH_2CH_2CH_2CH_2$—;
v) —$CH_2CH_2CH_2CH_2CH_2$—;
vi) —$CH_2CH_2CH_2CH_2CH_2CH_2$—;
vii) —$CH_2CH_2CH_2CH_2CH_2CH_2CH_2$—;
viii) —$CH_2CH_2CH_2CH_2CH_2CH_2CH_2CH_2$—;
ix) —$CH_2CH_2CH_2CH_2CH_2CH_2CH_2CH_2CH_2$—; and
x) —$CH_2CH_2CH_2CH_2CH_2CH_2CH_2CH_2CH_2CH_2$—.

One embodiment of this category relates to L units having the formula:
i) —$CH_2CH_2$—;
ii) —$CH_2CH_2CH_2$—; or
iii) —$CH_2CH_2CH_2CH_2$—.

Another category of L linking units relates to alkylene units having the formula:

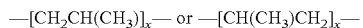

wherein $R^{2a}$ and $R^{2b}$ are each hydrogen or methyl; and the index m is from 1 to 10. Non-limiting examples of this category include:

i) —$CH_2CH(CH_3)$—;
ii) —$CH(CH_3)CH_2$—;
iii) —$CH(CH_3)CH_2CH_2CH(CH_3)$—;
iv) —$CH_2CH(CH_3)CH_2CH(CH_3)$—;
v) —$CH(CH_3)CH_2CH(CH_3)CH_2$—;
vi) —$CH_2CH(CH_3)CH(CH_3)CH_2$—;
vii) —$CH(CH_3)CH_2CH_2CH(CH_3)CH_2CH(CH_3)$—;
viii) —$CH_2CH(CH_3)CH_2CH(CH_3)CH_2CH(CH_3)$—;
ix) —$CH(CH_3)CH_2CH(CH_3)CH_2CH_2CH(CH_3)$—;
x) —$CH_2CH(CH_3)CH(CH_3)CH_2CH_2CH(CH_3)$—;
xi) —$CH(CH_3)CH_2CH_2CH(CH_3)CH(CH_3)CH_2$—;
xii) —$CH_2CH(CH_3)CH_2CH(CH_3)CH(CH_3)CH_2$—;
xiii) —$CH(CH_3)CH_2CH(CH_3)CH_2CH(CH_3)CH_2$—; and
xiv) —$CH_2CH(CH_3)CH(CH_3)CH_2CH(CH_3)CH_2$—.

A further category of L linking units relates to alkylene units comprising a $R^{2a}$ or $R^{2b}$ unit that is —$NH_3$ or —OH, non-limiting examples of which include:
i) —$CH_2CH(OH)$—;
ii) —$CH(OH)CH_2$—;
iii) —$CH_2CH(NH_2)$—;
iv) —$CH(NH_2)CH_2$—;
v) —$CH_2CH_2CH(OH)$—;
vi) —$CH_2CH(OH)CH_2$—;
vii) —$CH(OH)CH_2CH_2$—;
viii) —$CH_2CH_2CH(NH_2)$—;
ix) —$CH_2CH(NH_2)CH_2$—; and
x) —$CH(NH_2)CH_2CH_2$—.

The following are non-limiting examples of the substrates suitable as ligands for G-protein coupled receptors:

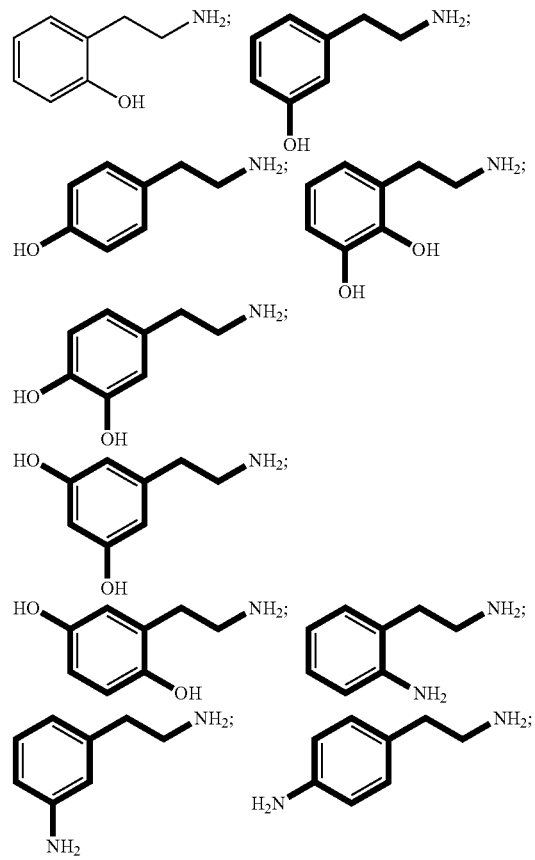

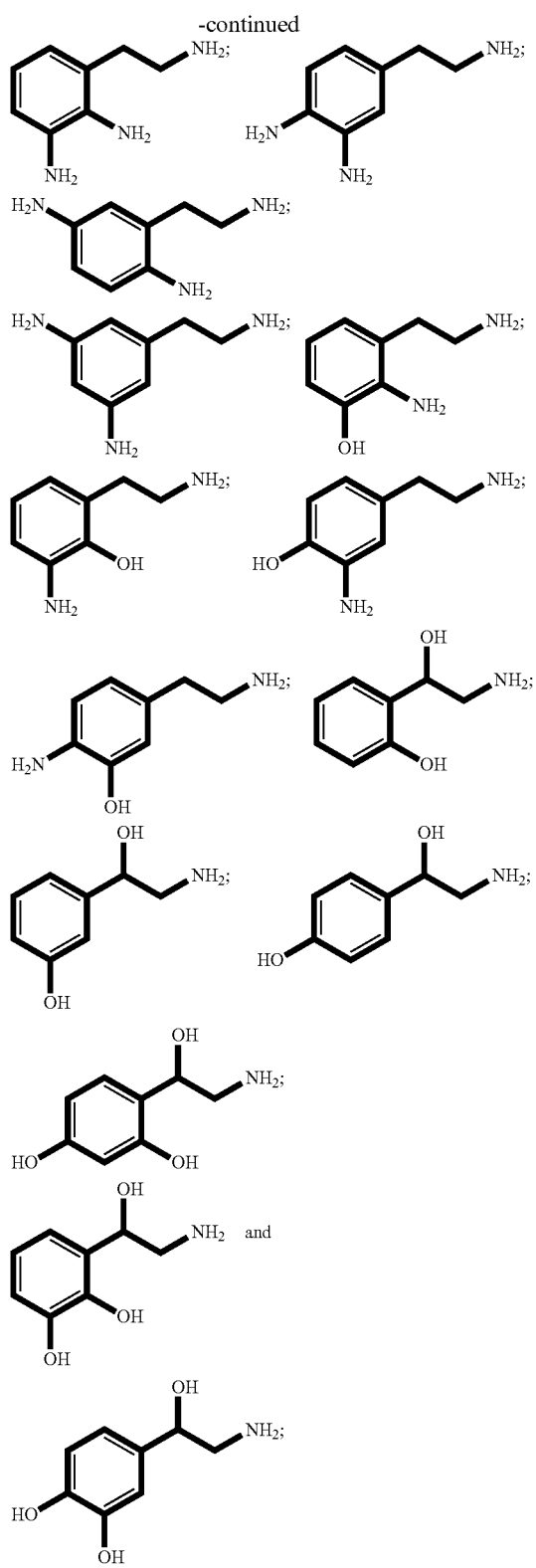

The disclosed substrates can be attached to the polymer by way of any reactive moiety, for example, hydroxyl or amino group. The following scheme outlines the possible adducts that are formed when noradrenalin is reacted with a carboxylate comprising polymer using carbonyl diimidazole as a catalyst.

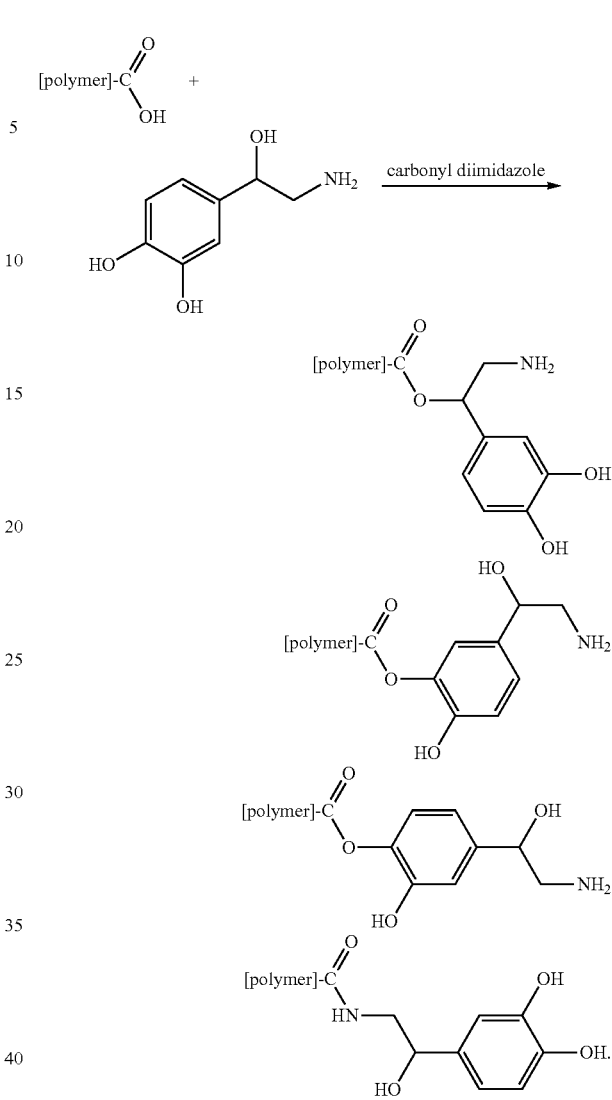

A composition comprising an adduct of Formula I attached to a marine/aquatic surface is disclosed. A composition comprising a signaling molecule for a G-protein coupled receptor (GPCR) linked to a marine/aquatic surface is disclosed. For example, a composition for deterring biofouling of a surface comprising an agonist of a β-adrenergic receptor linked to a marine/aquatic surface is provided.

A composition comprising an adduct of Formula I linked to a polymer is disclosed. A composition comprising a signaling molecule for a G-protein coupled receptor (GPCR) linked to a polymer is disclosed. For example, a composition for deterring biofouling of a surface comprising an agonist of a β-adrenergic receptor linked to a polymer is provided.

In a specific example of the composition, the polymer is methacrylic acid. As an alternative, the polymer can be 2-hydroxyethyl methacrylate.

Also provided is a non-toxic coating composition comprising (i) an adduct of Formula I; and (ii) a film forming agent, the adduct of Formula I being present in the composition in an amount effective to inhibit the attachment of biofouling organisms on a surface to which the composition is applied. In a specific example of the non-toxic coating composition, the adduct is noradrenalin, the noradrenalin being present in the composition in an amount effective to inhibit the attachment of biofouling organisms on a surface to which the composition is applied. Also provided is a non-toxic coating composition comprising (i) a signaling molecule for a GPCR; and (ii) a film forming agent, the signaling molecule for a GPCR being present in the composition in an amount effective to inhibit the attachment of biofouling organisms on a surface to which the composition is applied.

A "coating" refers to any temporary, semi-permanent or permanent layer or covering. A coating can be a gas, vapor, liquid, paste, semi-solid or solid. In addition a coating can be applied as a liquid and solidify into a hard coating. Examples of coatings include polishes, surface cleaners, caulks, adhesives, finishes, paints, waxes polymerizable compositions (including phenolic resins, silicone polymers, chlorinated rubbers, coal tar and epoxy combinations, epoxy resin, polyamide resins, vinyl resins, elastomers, acrylate polymers, fluoropolymers, polyesters and polyurethanes, latex). Silicone resins, silicone polymers (e.g. RTV polymers) and silicone heat cured rubbers are suitable coatings for use in the invention and described for example in the Encyclopedia of Polymer Science and Engineering (1989) 15: 204 et seq. Coatings can be ablative or dissolvable, so that the dissolution rate of the matrix controls the rate at which fouling deterrence agents are delivered to the surface. Coatings can also be non-ablative, and rely on diffusion principles to deliver a befouling deterrence agent to the surface. Non-ablative coatings can be porous or non-porous. A coating containing a biofouling deterrence agent freely dispersed in a polymer binder is referred to as "monolithic" coating. Elasticity can be engineered into coatings to accommodate pliability, e.g. swelling or shrinkage, of the surface to be coated.

The film-forming component of the composition can be any component or combination of components that is readily applied and adheres to the surface to be protected when the surface is submerged. The specific film-forming component to be selected for a particular application will vary depending on the material and construction of the article to be protected and the performance requirements thereof. After a surface is provided with a protective coating in accordance with this invention, the active ingredient (e.g., the adduct of Formula I) that is present in the coating comes in contact with biofouling organisms, thereby preventing their attachment (e.g., settling and/or cementation). A variety of synthetic polymers are useful for this purpose. Examples of suitable polymer resins include unsaturated polymer resins, vinyl ester, vinyl acetate, and vinyl chloride based resins and urethane based resins. Unsaturated polyester resins are formed from unsaturated acids and anhydrides, saturated acids and anhydrides, glycols, and glycol monomers. Preferred film-forming components are mixtures of natural rosin and vinyl chloride-vinyl acetate co-polymers. A commercial marine paint vehicle which is suitable for the practice of this invention is Amerlock 698, a product of Ameron International, Pasadena, Calif. Comparable marine paint vehicles are also available from Jotan, A S, Sandefjord, Norway.

Certain compounds exhibit increased stability and compatibility with chemicals used in standard coatings. Other preferred compounds result in a constant, sustained release. Still other compounds have a relatively short half-life after release rendering them particularly safe for widespread environmental use.

"Release rate" or "flux" refers to the rate of delivery or diffusion of a compound (e.g., GPCR signaling molecule) to and ultimately from a surface. The release rate may be constant or sustained over a period of time or may be variable. However, constant, controlled or sustained release rates are generally preferred. Steady state or sustained release may be effected by use of a reservoir membrane (i.e. a two layer coating in which one layer contains the active agent (e.g., GPCR signaling molecule) and the other creates a membrane through which the active agent can be released). The active agent could alternatively be microencapsulated within any of a variety of matrices for sustained release. Release rates of at least about 100, 150, 200 or 300 $\mu g/cm^{-2}$ $d^{-1}$, may be useful for temporary uses or uses that require reapplication. For more sustained applications, preferred release rates of less than about 100 $\mu g/cm^{-2}$ $d^{-1}$, more preferably less than about 75, less than about 50, less than about 25, less than about 10 or less than about 5.

"Sustained release" or "controlled release" refers to a relatively constant or prolonged release of a compound of the invention from a surface. This can be accomplished through the use of diffusional systems, including reservoir devices in which a core of a compound of the invention is surrounded by a porous membrane or layer, and also matrix devices in which the compound is distributed throughout an inert matrix. Materials which may be used to form lo reservoirs or matrices include silicones, acrylates, methacrylates, vinyl compounds such as polyvinyl chloride, olefins such as polyethylene or polypropylene, fluoropolymers such as polytetrafluorethylene, and polyesters such as terephthalates. The diffusional systems may be molded into a film or other layer material which is then placed in adherent contact with the structure intended for underwater use. Alternatively, the compounds of the invention may be mixed with a resin, e.g., polyvinyl chloride and then molded into a formed article, which integrally incorporates the compound to form a structure having a porous matrix which allows diffusion of the compound, or a functional portion thereof, into the surrounding environment. Microencapsulation techniques can also be used to maintain a sustained focal release of a compound of the invention. Microencapsulation may also be used for providing improved stability. The encapsulated product can take the form of for example, spheres, aggregates of core material embedded in a continuum of wall material, or capillary designs. The core material of a microcapsule containing a compound of the invention may be in the form of a liquid droplet, an emulsion, a suspension of solids, a solid particle, or a crystal. The skilled artisan will be aware of numerous materials suitable for use as microcapsule coating materials, including, but not limited to, organic polymers, hydrocolloids, lipids, fats, carbohydrates, waxes, metals, and inorganic oxides. Silicone polymers are the most preferred microcapsule coating material for treatment of surfaces. Microencapsulation techniques are well known in the art and are described in the Encyclopedia of Polymer Science and Engineering, Vol. 9, pp. 724 et seq. (1989) hereby incorporated by reference.

The phrase "effective amount" refers to an amount of the disclosed fouling deterrence compound that significantly reduces the number of organisms that attach to a defined surface (cells/mm$^2$) relative to the number that attach to an untreated surface. Particularly preferred are amounts that reduce the number of organisms that attach to the surface by a factor of at least 2. Even more preferred are amounts that reduce the surface attachment of organisms by a factor of 4, more preferably by a factor of 6, 8, 10, 15, 20 or more. In a specific example of a composition as disclosed herein, the noradrenalin is present in an amount from about 30 $\mu$M to about 100 $\mu$M on the polymer surface. There are methods which the concentration of the adduct of formula I or NA on a surface can be measured. For example, NA-conjugated polymers can be characterized using analytical surface analysis techniques such as X-Ray Photoelectron spectroscopy (XPS) and Static secondary ion mass spectroscopy (SIMS) to determine amount of NA present on the surface.

In the disclosed biofouling deterrent composition, the noradrenalin can be covalently attached to the film forming agent.

A paint comprising the biofouling deterrent composition is provided. In one example, the paint is formulated as a marine paint. See, for example Burgess et al. (2003); and Yebra et al. (2004).

A varnish comprising the biofouling deterrent composition is provided. In one example, the varnish is formulated as a marine varnish.

An anti-fouling surface comprising an effective amount of a GPCR signaling molecule is provided, wherein the signaling molecule or a biologically active fragment thereof is released from the surface. In the disclosed anti-fouling surface, the GPCR signaling molecule can be a β-adrenergic receptor agonist. In a more specific example of the anti-fouling surface, the β-adrenergic receptor agonist is noradrenalin.

In a further example of the anti-fouling surface, the release of the compound is a sustained release. In another example of the anti-fouling surface, the release of the compound is at a constant rate.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Effect of Surface Immobilized Noradrenalin Molecules on Adhering Hemocytes of the Eastern Oyster *Crassostrea virginica*

Materials and Methods
Materials: The iniferter N,N-(dimethylamino)dithiocarbamoylbenzyl(trimethoxy)silane (SBDC) was synthesized and purified as described previously. (de Boer, Simon et al. 2000; Rahane, Kilbey et al. 2005). Monomers, methacrylic acid (MAA; 99%, Aldrich) and 2-hydroxyethyl methacrylate (HEMA; ≥99%, Sigma,) were disinhibited by passing through a column containing activated, neutral aluminum oxide (Brockmann I, Acros) and collected in a clean and dry scintillation vial. The disinhibited monomer was used immediately for polymerization. 1,1-carbonyldiimidazole (CDI; 97%, Acros), DL-noradrenaline (NA; Sigma), boric acid (≥99.5%, Fisher), sodium tetraborate (99.5-105.0%. Fisher), sodium phosphate dibasic (≥99%, Riedel-de Haën), anhydrous dimethyl sulfoxide (DMSO; ≥99.7%, Acros), anhydrous dimethyl formamide (DMF; ≥99.8%, Fluka), ethanol (≥99.5%, Fisher) and acetone (≥99.5%, Fisher) were used as received.

First, self-assembled monolayers (SAM) of the iniferter SBCD were deposited on 1 cm×1 cm glass substrates cut from transparent microscope slides, as described previously. (Rahane, Kilbey et al. 2005; Harris and Metters 2006) For polymerizations, either MAA or HEMA in pure form or as 75% solution in deionized water was used. MAA and HEMA were selected for monomers since they are very conducive for grafting from surfaces and do not form crosslinked gels under the current experimental conditions. In addition, both MAA and HEMA provide reactive —COOH and —OH side groups respectively throughout the polymer chain length, which can be utilized to conjugate the biomolecule.

Photopolymerization: The monomer solution was degassed in a Schlenk flask by freeze-vacuum-thaw cycles to remove all dissolved oxygen from the solution, as oxygen is a known inhibitor of free radical polymerization.

Photopolymerizations were conducted in a mask aligner system (Hybralign Series, OAI) the 365 nm UV beam was kept at a constant intensity of 25 mW/cm$^2$. One SAM substrate was placed in a specially fabricated Teflon exposure cell and a Viton o-ring was placed around the substrate (see FIG. 1). The exposure cell was placed on the mask aligner. A hood with a transparent glass window was closed on top to form a polymerization chamber which was continuously purged with $N_2$. The hood was opened and about 10 drops (~100 µl) of degassed monomer solution were placed on each substrate with a glass syringe. The hood was closed and the platform was raised vertically so that the o-rings touched the glass window forming an air tight seal (see FIG. 1). Care was taken that the entire substrate was covered with monomer solution and no air bubbles formed over the substrate surface. The UV beam was switched on for 10 to 60 min, depending on the requirement. After exposure, the substrates were rinsed with ethanol and sonicated in ethanol for 40 to 60 min to remove any unreacted monomer and ungrafted polymer debris. The substrates were rinsed with ethanol, dried under $N_2$ gas flow and stored in clean, dry test tubes.

Characterization of Polymer Grafted Surfaces: The presence and thickness of the grafted polymer on the glass substrates was measured using atomic force microscopy (AFM). Post-polymerization, polymer was mechanically removed along a narrow strip (~200 µm wide) between two opposite edges of the substrate using a piece of aluminum. The substrates were sonicated in ethanol to remove the polymer debris, dried with $N_2$ gas and were scanned with an atomic force microscope. Scanning was done on a Veeco Dimension 3100 AFM in Contact Mode using a DNP cantilever with the following scan parameters: Scan Size: 60 to 80 µm; Aspect Ratio: 16:1; Scan Rate: 1 Hz; Lines/Scan: 512. The difference in height between the polymer and glass surface was used to calculate the polymer layer thickness.

At least three samples each with MAA and HEMA grafting were kept aside without any further modification for use as controls in cell culture. The remaining MAA and HEMA grafted substrates (15-20 of each) were used for conjugation of NA as described below.

Figure 2:
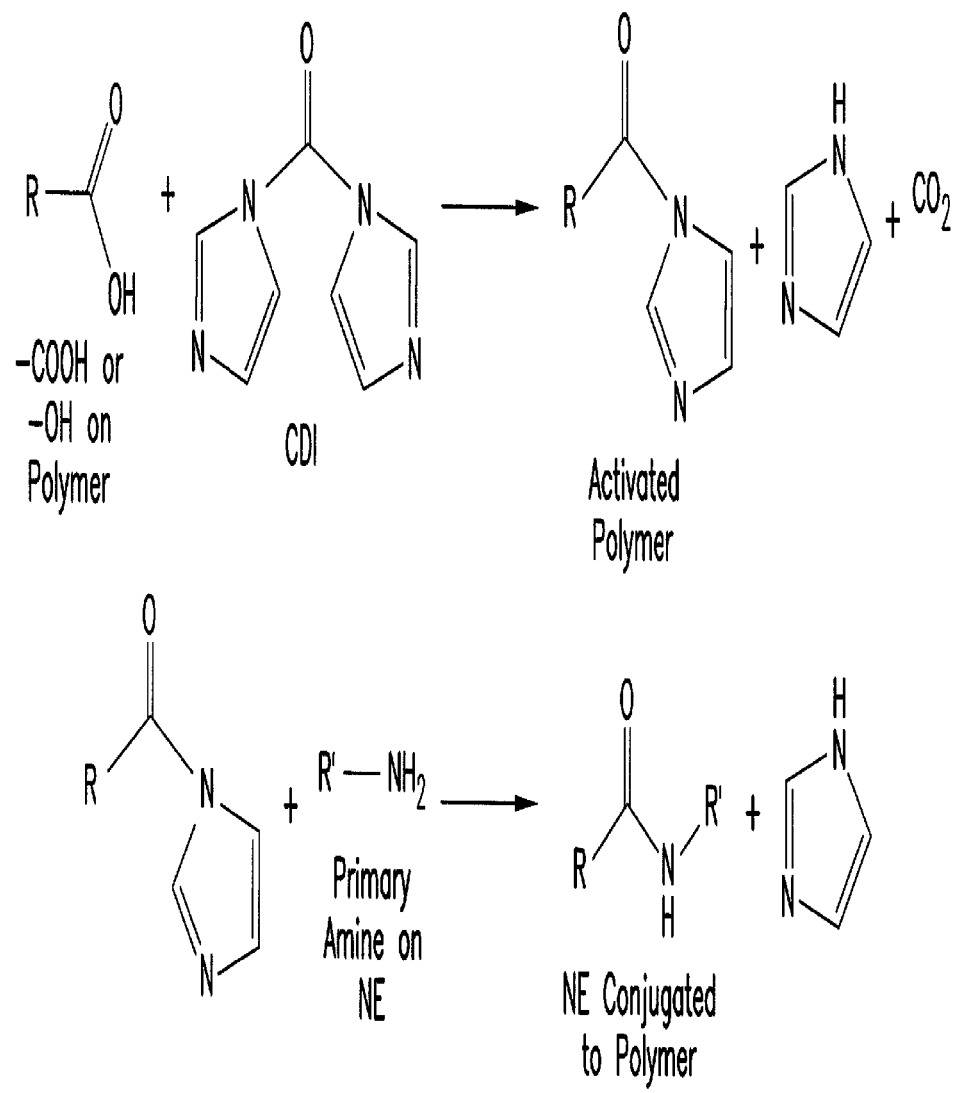
FIG. 2 shows the two chemistries used to conjugate noradrenalin to —COOH or —OH groups on the polymer chains. A: Carbonyldiimidazole (CDI) chemistry used to conjugate NA to —COOH groups of pMAA or —OH groups of pHEMA. B: Disuccinimidyl chemistry used to conjugate NA to —OH groups of pHEMA.

Conjugation of DL-Noradrenaline: Covalent conjugation of NA to carboxyl —COOH groups of MAA and hydroxyl —OH groups of HEMA was carried out using the carbonyldiimidazole chemistry (see FIG. 2A). Scintillation vials were dried in a vacuum oven at 100° C. for 1 hr prior to use to reduce presence of moisture during the activation step. The MAA and HEMA grafted substrates were placed in individual scintillation vials, sealed with silicone septum screw caps and purged with $N_2$ gas for at least 15 min. Three milliliters of 30 mg/ml CDI solution in anhydrous DMSO was added to each vial and allowed to react for 24 hrs on an orbital shaker. The substrates were then rinsed with acetone and sonicated in anhydrous DMSO for 15 min to remove reaction products (see FIG. 2A) and any unreacted CDI. The samples were dried with $N_2$ and placed in individual clean, dry scintillation vials with silicone septum screw caps and purged with $N_2$. Three milliliters of 1 mg/ml noradrenaline solution (NA) in pH 8.0 borate buffer were added to each vial. The conjugation reaction continued for 24 hrs in dark under gentle agitation. The substrates were rinsed and sonicated in pH 8.0 buffer for 15 min to remove reaction products (see FIG. 2). They were dried with a $N_2$ and stored in clean, dry test tubes at $-4°$ C. Substrates were used for cell culture within 3 days of NA conjugation.

Figure 3:
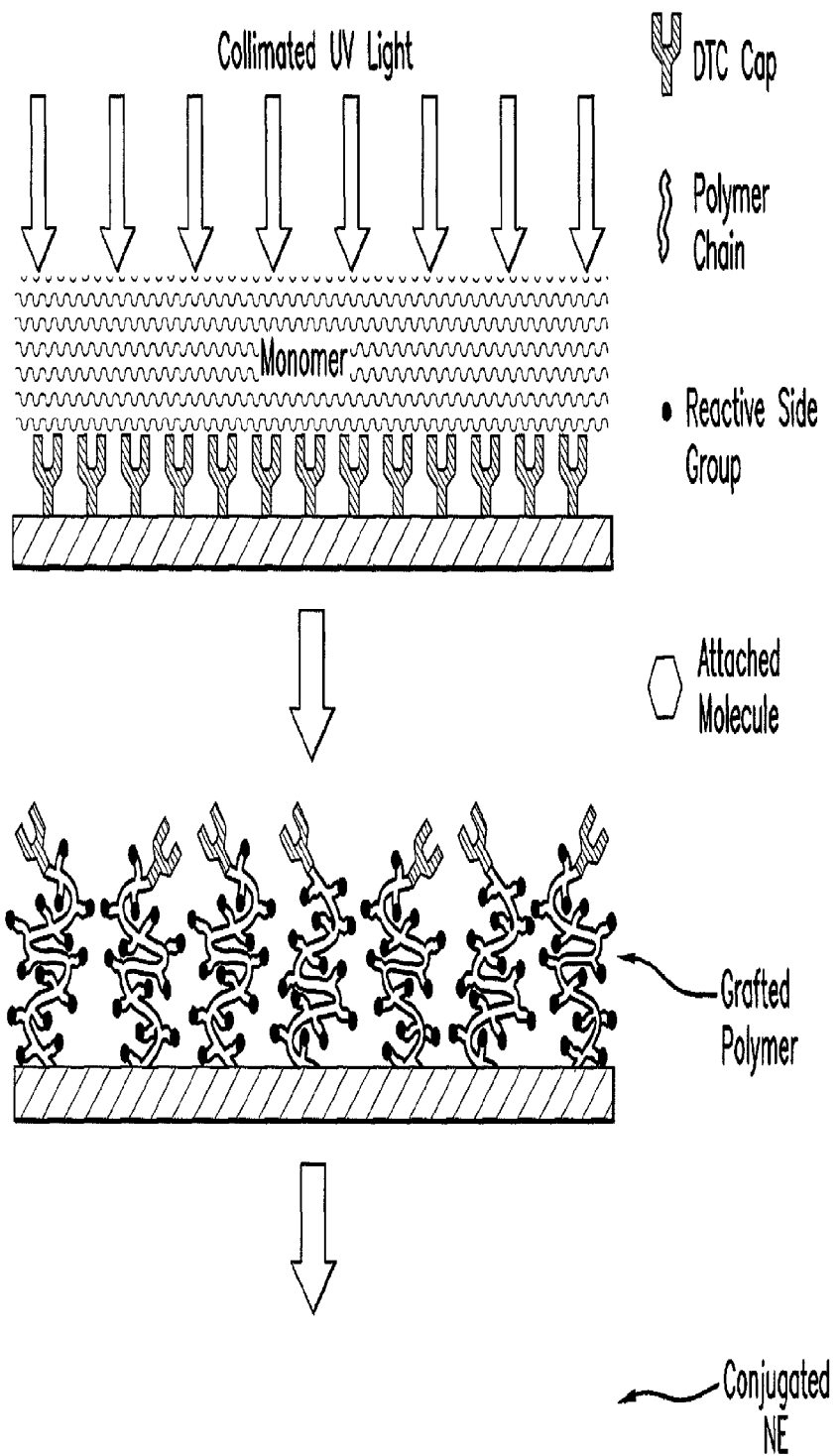
FIG. 3 shows creation of immobilized bioactive fouling deterrent surfaces using photopolymerization and covalent conjugation.

This entire process from photopolymerization from glass substrates to the final bioactive substrates with covalently immobilized NA is illustrated in FIG. 3. The small red lines indicate the —COOH and —OH reactive side groups of MAA and HEMA respectively to which NA was covalently conjugated using the CDI chemistry mentioned above.

Oyster Culture

Adult Eastern Oyster Crassostrea virginica were purchased from Pemaquid Oyster Company Inc. (Waldoboro, Me.). After receiving, the oysters were held in a 180 gallon (681 liter) tank at $18°$ C. in artificial sea water at 31% salinity with saturating levels of dissolved oxygen. The animals were fed twice a week with Shellfish Diet 1800® (Reed Mariculture Inc. Campbell, Calif.). To obtain oyster hemocytes, the oyster's shell was notched with a cement saw to enable hemolymph extraction from the adductor muscle. A 22 gauge needle affixed to a disposable syringe was inserted into the adductor muscle and approximately 1 ml of hemolymph was withdrawn (Lacoste, Cueff et al. 2002).

Definition of Control Surfaces

To assess the effect of NA-conjugated polymer surfaces on adhering hemocytes a variety of control surfaces were tested in parallel to NA-conjugated polymers. Control surfaces included glass coverslips, MAA and HEMA polymer grafted surfaces without NA conjugation which from here on will be referred to as control surfaces. As hemocyte response to all of the control surfaces was similar, data presented here are representative images from above mentioned control surfaces.

Viability of the Hemocytes Assessed by Calcein-AM Staining

Oyster hemocytes were obtained as described earlier; ~500 μl of hemolymph was seeded on control surfaces, NA-HEMA and NA-MAA polymer surfaces. Hemocytes were allowed to adhere and settle on substrates at $18°$ C. for 45 minutes. Substrates were then washed twice for three minutes each with molluscan PBS (PBS osmolality was matched to the hemolymph) to remove hemolymph and unattached cells. Each substrate was then placed in 60×15 mm petri dishes (Fisher Scientific) containing molluscan PBS at $18°$ C. Calcein-AM is a fluorophore coupled with an acetomethoxy ester. Living cells possessing esterases take in the dye and cleave the AM moiety of the dye, rendering it fluorescent. To the substrates 10 μm solution of Calcein-AM (Invitrogen) in molluscan PBS was added and incubated for 20 minutes in dark. Substrates were then washed twice for five minutes each with molluscan PBS to remove Calcein-AM dye. Hemocytes were counterstained with a 300 nM solution of 4',6-diamidino-2-phenylindole dihydrochloride or DAPI (Invitrogen cat#1306) for five minutes. Substrates were washed twice for five minutes each with molluscan PBS to remove excess DAPI. Fluorescence microscopy was performed on the substrates using Carl Zeiss Axiovert-135 inverted microscope (Carl Zeiss Inc.) with appropriate filter sets for Calcein-AM and DAPI with a 40× oil immersion objective. Digital images were recorded using a Zeiss Axiocam MRC-5 camera.

Effect of NA-Conjugated Polymer Surface on Hemocyte Cytoskeleton

Oyster hemocytes were obtained as described earlier and incubated on the control, NA-MAA and NA-HEMA surfaces. Hemocytes were allowed to adhere and settle on substrates at $18°$ C. for 45 minutes. Substrates were then washed twice for three minutes each with molluscan PBS. Cells were then fixed on substrates with 4% paraformaldehyde made up in PBS for 30 minutes followed by three PBS washes for five minutes each. To permeablize the cells, substrates were incubated with a 0.1% solution of Triton-X 100 for five minutes followed by two washes of three minutes each. Substrates were then incubated in a 50 □M solution of FITC-Phalloidin (Sigma-Aldrich) for 30 minutes, followed by two washes of five minutes each to remove excess phalloidin. Substrates bearing hemocytes were then counterstained with DAPI and fluorescence microscopy was performed as previously described.

Assessing the Ability of NA-Conjugated Polymer Surface to Induce Apoptosis in Adhering Hemocytes Hemocytes were obtained as previously described and incubated on control, NA-MAA and NA-HEMA. Substrates bearing cells were analyzed using Vybrant Apoptosis Assay Kit #11 (Invitrogen). The assay detects translocation of phosphatidylserine from the inner leaflet of the plasma membrane to the outer leaflet. The assay was performed according to the protocol accompanying the kit and is briefly summarized here. Following incubation, substrates bearing hemocytes were incubated with the mitochondrial dye MitoTracker Red (supplied with the kit) after a by a brief wash substrates were incubated with annexin binding buffer and Alexa Fluor 488 Annexin-V (supplied with the kit) for 30 min, fluorescence microscopy was carried out as previously described.

Visualizing the Interaction Between Hemocytes and NA-Conjugated Polymer Surfaces Using Scanning Electron Microscopy Hemocytes were incubated on control, NA-MAA and NA-HEMA polymer surfaces as previously described. Hemocytes were then fixed on the substrates using a mixture of 2.5% glutaraldehyde and 2% paraformaldehyde (Electron Microscopy Sciences EMS, Hatfield, Pa.) made up in 100 mM sodium cacodylate buffer (EMS) for 30 minutes at $4°$ C. Substrates were then washed three times for ten minutes each. Cells were then post fixed using a 1% solution of osmium tetroxide (EMS) made up in sodium cacodylate buffer for twenty minutes. Following post fixation, cell bearing substrates were washed with deionized water three times for ten minutes each. To dehydrate the cells, substrates were taken through a graded ethanol series of 25%, 50%, 75%, 80%, 90%, 100%. In the graded series, dehydrations between 50%-100% ethanol were carried out at $0°$ C. to minimize extraction. Samples were transferred to a chamber of critical point dryer (CPD) in ethanol. Substrates were subjected to three washes of liquid $CO_2$ five minutes each to remove ethanol from the sample. Critical point drying was carried out at 1072 psi at $31°$ C. After CPD, substrates were mounted on aluminum stubs using double sided carbon tape, and sputter coated using a Denton sputter coater with a gold-palladium target. Substrates were imaged using Hitachi Field Emission-S4800 and Hitachi-S3400 scanning electron microscopes (SEM).

Figure 4A:
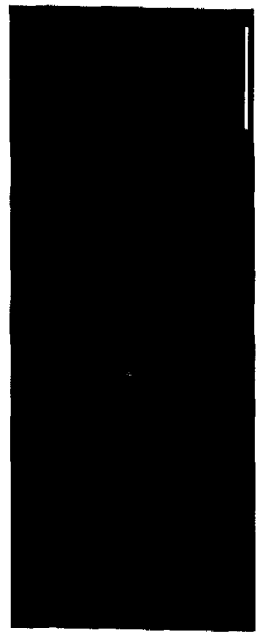
FIG. 4 shows the effects of NA-conjugated polymer surface on the cytoskeletal structure and viability of adhering hemocytes. A) Fluorescent micrograph of hemocytes incubated on control surfaces and labeled with Calcein-AM and DAPI. Green fluorescence indicates adhering cells are healthy and viable. B) Fluorescent micrograph of hemocytes incubated on control surfaces labeled with Alexa Fluor-488 phalloidin labeling F-actin. There is no evidence of the any stress or abnormalities on the cytoskeletal structure of the adhering hemocytes. C), D) Fluorescent micrograph of hemocytes incubated on NA-MAA polymer surfaces labeled with Alexa Fluor-488 phalloidin and DAPI, labeling F-actin and nuclei respectively. Hemocytes adhering to NA-MAA polymer show abnormal and stressed cytoskeleton (arrowheads). Disintegrating cells and abnormal accumulation of actin is clearly seen (arrows). E) Fluorescent micrograph of hemocytes incubated on NA-HEMA polymer surfaces labeled with Alexa Fluor-488 phalloidin and DAPI. Pronounced cytoskeletal disintegration is evident; as a result adhering hemocytes have abnormal morphologies (arrows). F) Fluorescent micrograph of hemocytes incubated on NA-HEMA polymer surfaces labeled with Alexa Fluor-488 phalloidin and DAPI. Enucleated hemocytes with disintegrated cytoskeletons can be seen (arrows). As a consequence of cytoskeletal deterioration nuclei are released from the hemocytes and can be observed extracellularly (arrowheads).

Results:
NA-Conjugated Polymer Surfaces Adversely Affect the Cytoskeleton of Adhering Hemocytes
Hemocytes adhering to the control surfaces label positive for calcein-AM. Cells adhering to control surfaces show bright Calcein-AM labeling and fail to label for DAPI (FIG. 4A), indicating that polymer surfaces alone do not exert any deleterious effects on the adhering cells. Hemocytes adhering to NA-MAA or NA-HEMA surfaces fail to exhibit any fluorescence from calcein-AM labeling and label positive for DAPI, indicating that cell viability is compromised upon adhering to these surfaces.

Figure 4C:
Figure 4E:
Figure 4B:
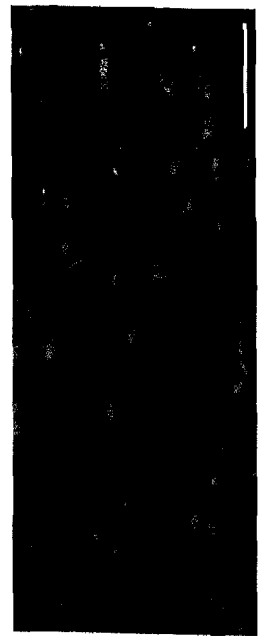
Figure 4D:
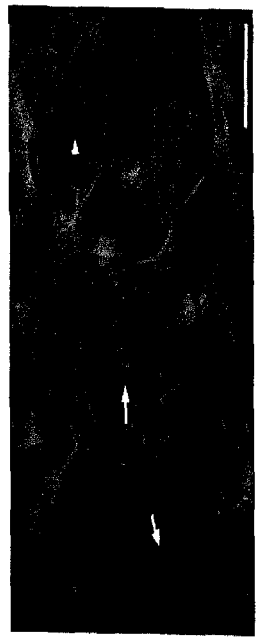
Figure 4F:

Polymer surfaces are known to exert an effect on the cytoskeletal structure of the adhering cells (Shunji Nagahara 1996; Masayuki Yamato 1999; Shin-Ichi Sawada 2006). The effect of NA-conjugated polymer surface was evaluated by labeling actin filaments of the adhering hemocytes. Cells adhering to the control surfaces show a diffused pattern of actin filaments and an absence of stress filaments (FIG. 4B). Hemocytes adhering to NA-MAA surface show stressed actin filaments (FIG. 4C-D). Abnormal localization of actin and disintegrating cell membranes are also seen in adhering hemocytes (FIG. 4C-D arrows). NA-HEMA surface also exerts similar effect on the actin filaments of the adhering hemocytes. Cells adhering to NA-HEMA surface can be seen to have undergone advanced disintegration (FIG. 4E-F). Degradation of cytoskeleton seems to have lead to loss of nuclei from adhering hemocytes. The enucleated hemocytes with extracellular nuclei can be seen in FIG. 4F. Taken together this data suggests that MAA and HEMA surfaces alone do not exert any adverse effects on the cytoskeleton of the adhering cells. NA conjugated HEMA/MAA polymer surfaces induce cytoskeletal degradation in adhering hemocytes.

Figure 5A:
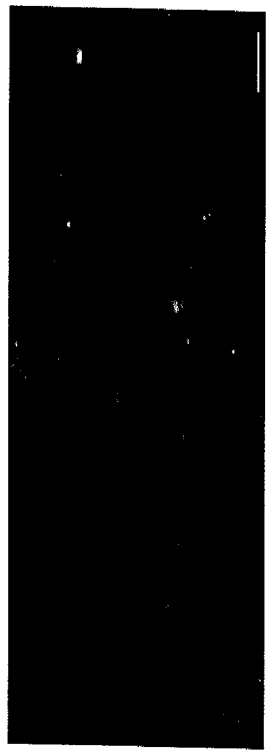
FIG. 5 shows the interaction between hemocytes and NA-conjugated polymer surfaces using Annexin-V apoptosis assay. A) Hemocytes incubated on control surfaces labeled with Alexa Fluor-488 Annexin-V and MitoTracker Red. Hemocytes label positive for MitoTracker red indicating viable and healthy cells and an absence of apoptosis. B) Hemocytes incubated on NA-conjugated polymer surfaces labeled with Alexa Fluor-488 Annexin-V and MitoTracker Red. Hemocytes label positive for Annexin-V indicating that cells are undergoing apoptosis, as cells are undergoing apoptosis there is an absence of mitochondrial labeling by MitoTracker Red. This is a representative micrograph from NA-MAA polymer surface. Cells show similar pattern of labeling on NA-HEMA polymer surface. Scale bar: A, B=10 µm.
Figure 5B:
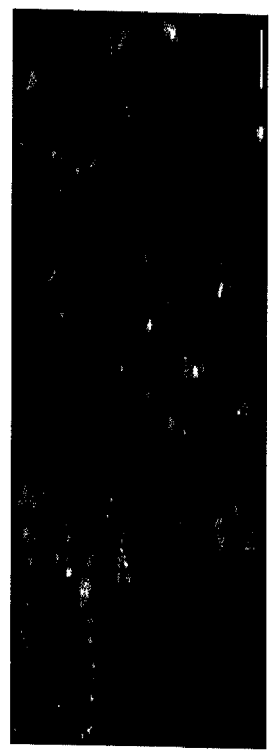

To assess the effects of NA-conjugated polymer surface on cell viability, cells adhering on control and NA-conjugated polymer surfaces were analyzed with the Annexin-V apoptosis assay. Hemocytes incubated on the control surfaces display intense staining with MitoTracker Red indicating that the cells are viable and healthy. These cells fail to label for Annexin-V indicating an absence of apoptosis (FIG. 5A). Hemocytes incubated on NA-MAA and NA-HEMA polymer surfaces fail label for MitoTracker Red but label positive for Annexin-V, indicating that the cells undergo apoptosis as a consequence of interaction with NA conjugated polymer surfaces (FIG. 5B).

Figure 6A:
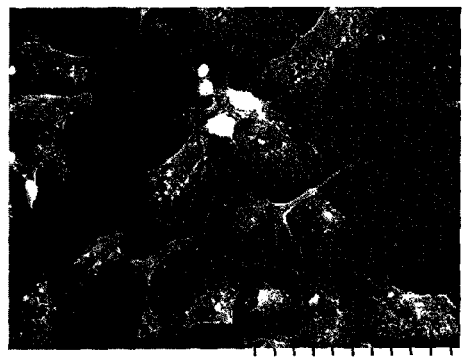
FIG. 6 shows the interaction between hemocytes and NA-conjugated polymer surfaces A) Scanning electron micrograph of hemocytes adhering to control surfaces showing normal morphology and uncompromised cell membranes, indicating that underlying surface does not exert any deleterious effects on adhering cells. B-D) Hemocytes incubated on the NA-MAA polymer surfaces exhibit compromised cell membranes, where cell morphology can be seen disintegrating around the cell's periphery. The area inset square box is observed under higher magnification in D. Disintegrated cell membranes of the two adjacent cells are clearly visible. C-E) Hemocytes incubated on NA-HEMA polymer surfaces. Similar to NA-MAA surfaces, hemocytes adhering to NA-HEMA surfaces show pronounced deterioration. A hemocyte with a disintegrated morphology is seen (arrows). Area inset box is observed under higher magnification in E, the hemocyte is disintegrating in small fragments around the periphery. F) Adjacent hemocytes adhering to NA-HEMA polymer surface, one of the hemocytes is disintegrating while the adjoin cell appears to be intact. Cytoskeletal destruction is evident in hemocytes adhering to NA-conjugated polymer surfaces.
Figure 6B:
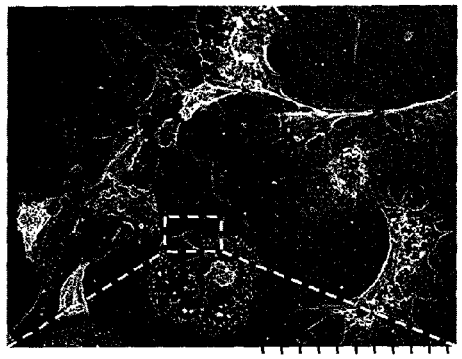
Figure 6C:
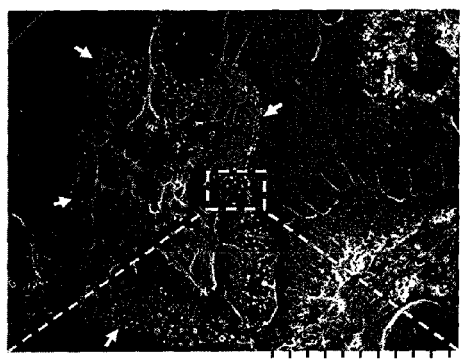
Figure 6D:

Hemocytes incubated on NA-MAA surfaces exhibit abnormal morphology, the cell membranes can be seen disintegrating or blebbing off towards the periphery of the cells, perhaps an indicator of terminal stages of apoptosis (Lacoste, Cueff et al. 2002) (FIG. 6B-D).

Figure 6E:
Figure 6F:
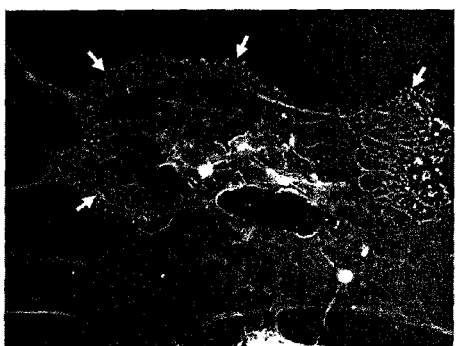

Cells incubated on NA-HEMA exhibit similar effects as those incubated on NA-MAA surface. Disintegrating cell membranes resembling apoptotic bodies are clearly visible (FIG. 6C-E). An indicator that NA-conjugated surfaces induce apoptosis in adhering cells, with two adjacent hemocytes adhering to NA-MAA surface, one cell can be seen disintegrating while the other remains intact (FIG. 6F). These results in accord with earlier results indicate that NA-conjugated polymer surface induce apoptosis in adhering cells, consequence of which cells with disintegrating membranes can be seen on the surfaces.
Effect of Treatment of Oyster Larvae with Micromolar Concentrations of Noradrenalin
Treatment of larvae results in complete disruption of the settling behavior and cementation. Oyster larvae metamorphose into adult oysters without cementation. These oysters viable and develop normally into adults.

Example 2

Settlement Inhibition of the Cyprid Larvae the of Barnacle (*Balanus amphitrite*) by NA Methods:
Barnacle cyprids were challenged with 30-100 micro molar ranges of noradrenalin. Barnacle cyprids were monitored and assayed over period of 120 hours (5 days). Cyprid metamorphosis was imaged at 24, 48, 96, 120 hour intervals. Images were taken at each intervals and samples preserved for SEM analysis. On the last day of the experiments the metamorphosed barnacles were assayed for viability. The experiments were repeated 4 times with 3 replicates per experiment.
Results:
Treatment of cyprids with noradrenalin prevented them from settling or attaching to a surface. The treatment did not effect the viability of the cyprids, and the treated cyprids metamorphosed into adults.

Post NA treatment, either by flash induction or by incubating the cyprids in ASW containing NA. The cyprids stopped swimming and sank to the bottom of the petri dishes and with momentary movements of the thoracopods and the antennules. This observation is analogous with Coon, Bonar et al 1986, where NA treated oyster larvae stopped swimming and sank to the bottom of petri dishes. The noted "searching behavior" (Hisashi Yamamoto 1999) of the cyprids was also lost after NA treatment and the cyprids did not attach or cement to substratum. Twenty-four hours (hr) post NA treatment, cyprids did not display any signs of ecdysis. The onset of ecdysis was observed between 24 hr and 48 hr post NA treatment. Metamorphosing juvenile barnacles were seen encased in bivalve cyprid carapace. The pumping action of the thorax similar to beating of cirri was also observed (Glenner and Høeg 1993). Seventy-two hours post NA treatment the metamorphosing barnacles displayed recognizable features such demarcations between the base plates and the opercular plates. Some ecdysing barnacles were still encased in cyprid carapaces while others had shed the bivalve carapace. The cyprids that had shed carapace were presumed to have 'grown' out of it as opposed to have shed carapace voluntarily as observed in untreated attached cyprids (Glenner and Høeg 1993). A well demarcated operculum from the base plate was observed in juvenile barnacles. Ninety-six hours post NA treatment, the operculum with tergal and scutal plates is well demarcated from the wall plates. In contrast, control barnacles can be seen fully calcified with well recognizable wall and opercular shell plates at around 24-48 hr post settlement. Thus the NA treated cyprids took 96 hr to fully metamorphose and calcify but remained unattached and un-cemented to the substratum.

Example 3

Characterization of NA Conjugation to Polymer and Understanding the Effect of Antibody Blocked Surface Conjugated Noradrenalin Molecules on Adhering Hemocytes of the Eastern Oyster *Crassostrea virginica*

Methods
Using DSC Chemistry to Conjugate NA Molecules to HEMA Surfaces
For the following experiments, NA was conjugated to —OH groups on pHEMA using the DSC chemistry (FIG. 2B).

Scintillation vials were dried in a vacuum oven at 100° C. for 1 hr prior to use to reduce presence of moisture during the activation step. pHEMA grafted samples were placed individually in the dried vials. Activation solution was prepared by dissolving 4 mg/ml disuccinimidyl carbonate (DSC) in anhydrous dimethylformamide (aDMF) followed by addition of a molar equivalent amount of dimethylaminopyridine (DMAP). 3 ml of this DSC+DMAP solution was added to each vial and sealed with caps. Post activation for 6 h on an orbital shaker, DSC+DMAP solution was removed from the vials and 3 ml of fresh aDMF was added. Samples were washed on a shaker for 10 mins to remove unreacted components and reaction byproducts. Samples were then rinsed with deionized water to wash away DMF. Samples were immediately placed in clean scintillation vials each containing 3 ml of 1 mg/ml noradrenalin (NA) solution in pH 8.0 phosphate buffer. NA conjugation took place on an orbital shaker overnight. Samples were rinsed with buffer. and sonicated for 15 min to remove unreacted NA and reaction by products (FIG. 2B). Samples were finally rinsed with deionized water, dried under $N_2$ gas flow and stored in sealed test tubes.

Characterization of NA-Conjugated HEMA Surfaces Using AFM

Thickness of the pHEMA polymer layers was measured using atomic force microscopy (AFM) before beginning the conjugation procedure. AFM measurement scans were repeated on NA conjugated HEMA substrates and control substrates treated with DSC but without NA. The pre- and post-conjugation thicknesses were compared. Conjugation of any molecule to surface grafted polymer brushes increases the local steric hindrance which causes the polymer chains to stretch, which translates into increase in measured polymer layer thickness.

Characterization of NA-Conjugated HEMA Surfaces Using XPS

X-ray photoelectron spectroscopy (XPS) was carried out using a Kratos Axis 165 system with an aluminum Kα source run at 15 kV and 15 mA. Pass energy of 80 eV was used for hemispherical analyzer run on survey scans and 20 eV for high-resolution scans. For XPS characterization, two sample groups were used where NA was conjugated to HEMA. The samples from the two groups were as follows. A) NA conjugation using DSC chemistry which included, i) NA+HEMA surface, HEMA control surfaces taken through DSC conjugation without any NA, and iii) a unmodified HEMA surface. B) NA conjugation using CDI chemistry (described in Example 1) which included, i) NA+HEMA surface, HEMA control surface taken through CDI conjugation without any NA, and iii) a unmodified HEMA surface.

Anti-Noradrenalin Antibody Treated NA+pHEMA Surfaces

To determine if the covalently conjugated NA molecules are indeed responsible for inducing apoptosis in adhering hemocytes, NA conjugated to pHEMA substrates was blocked using an anti-noradrenalin antibody (Advanced targeting systems). NA+pHEMA substrates were incubated with a 1:500 dilution of the anti-NA antibody in PBS overnight on a shaker. For control purposes NA+pHEMA polymer substrates were incubated in PBS overnight on a shaker without anti-NA antibody. Post incubation surfaces were washed thrice for 5 minutes each.

Oyster hemocytes were obtained as described in Example 1. Approximately 5000 of hemolymph was aliquoted on NA+pHEMA substrates. Hemocytes were incubated at 18° C. for 45 minutes. To remove unattached cells, substrates were washed twice for three minutes each with molluscan phosphate buffer saline (PBS) (PBS osmolality was matched to the hemolymph). Each substrate was then placed in 60 mm×15 mm petri dishes (Fisher Scientific) containing molluscan PBS at 18° C. Ten micromolar solution of Calcein-AM (Invitrogen, Carlsbad, Calif., cat#C3099) in molluscan PBS was added to substrates and incubated for 20 minutes in dark. Substrates were then washed twice for five minutes each with molluscan PBS to remove excess dye. Calcein-AM is a fluorophore coupled with an acetoxy-methyl ester. Living cells possessing esterase enzymes take in the dye and cleave the AM moiety of the dye rendering it fluorescent. Hemocytes were counterstained with a 300 nM solution of 4',6-diamidino-2-phenylindole dihydrochloride or DAPI (Invitrogen) for five minutes. Substrates were washed twice for five minutes each with molluscan PBS to remove excess DAPI. Observations were made using the Nikon-TiE microscope equipped with an appropriate filter set for DAPI and Calcein-AM. After the viability assay, same samples were processed for the cytoskeletal assay as described in Example 1.

Control experiments were run with unmodified HEMA substrates, and HEMA substrates taken through both the CDI and DSC conjugation reaction without the addition of any NA.

Results

AFM Characterization of NA+pHEMA Surfaces

Figure 7:
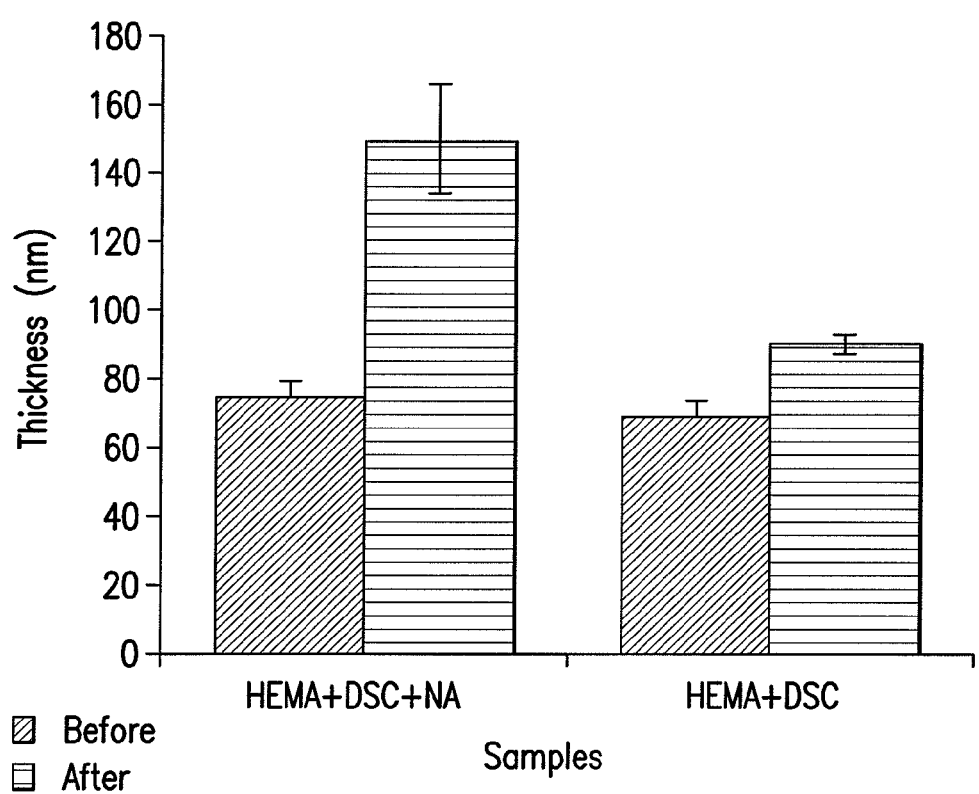
FIG. 7 shows thickness of the pHEMA polymer layers measured using atomic force microscopy (AFM) before and after the NA conjugation procedure. A significant increase in thickness is observed after NA conjugation which verifies covalent conjugation of NA to polymer chains. Control substrates subjected to conjugation procedure without NA added do not show a significant increase in thickness.

A significant increase in polymer layer thickness was observed when NA was conjugated to the pHEMA chains (FIG. 7). No such significant increase was observed when the same procedure was repeated for pHEMA samples without adding NA during the conjugation procedure (FIG. 7). This clearly indicated that NA was successfully conjugated to the pHEMA chains using the DSC chemistry. Since all the samples were subjected to ultrasonication post-NA conjugation, change in height due to any adsorbed NA was ruled out.

XPS Characterization of NA+pHEMA Surfaces

Figure 8A:
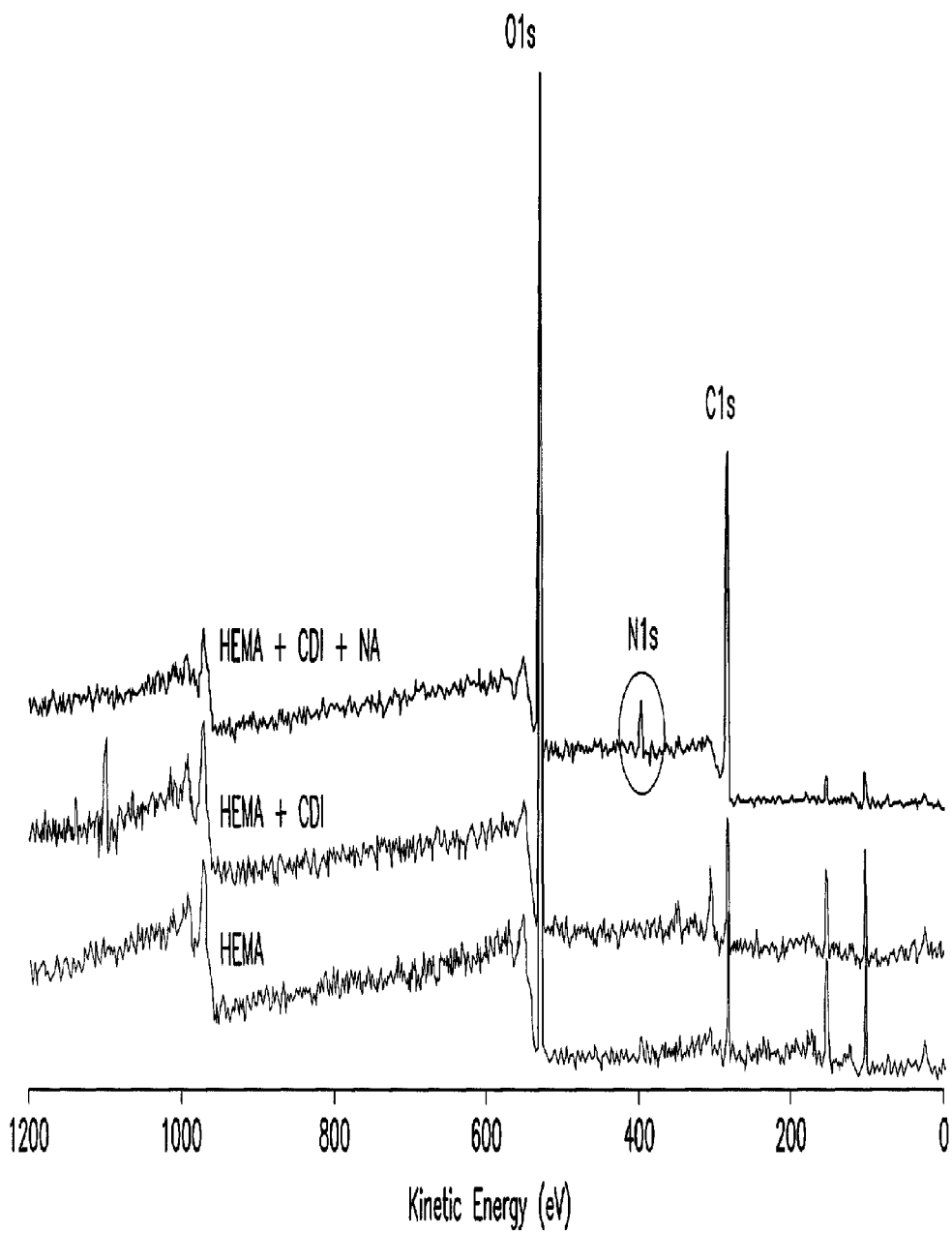
FIG. 8 shows XPS characterization of NA conjugated substrates. A: Comparison between XPS spectra of the samples from the CDI chemistry group. Nitrogen peak (encircled) is only seen on the NA-conjugated surface's spectrum and is absent in all the control surfaces' spectra. B: A comparison between the XPS spectra from the DSC chemistry group. Similar to the CDI group, the nitrogen peak (encircled) is only seen on the NA-conjugated surface's spectrum and is absent in all the control surfaces spectra.
Figure 8B:
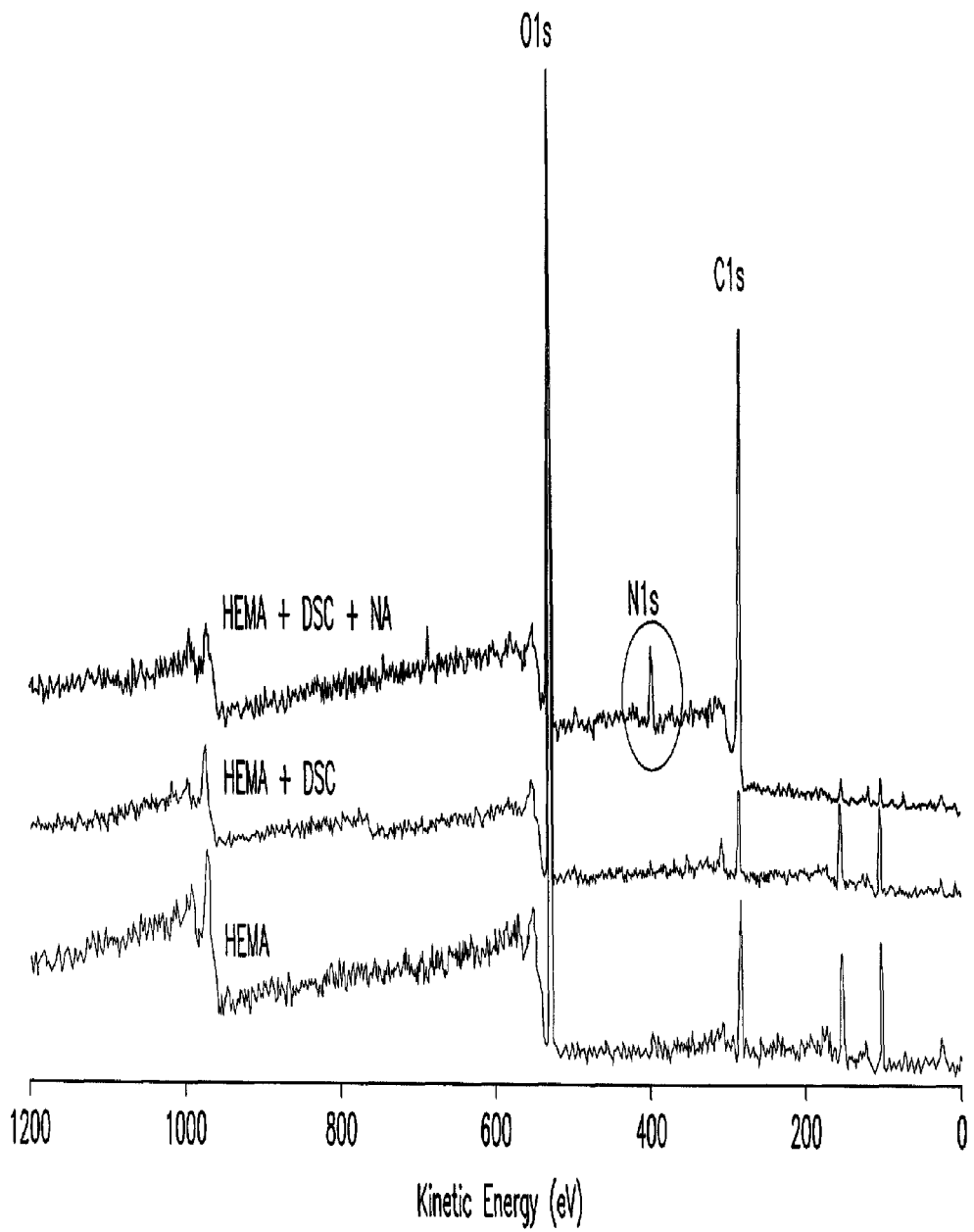

A nitrogen peak was observed in the XPS spectra of NA conjugated HEMA surfaces using both the CDI and DSC chemistry (FIG. 8). XPS spectra of control surfaces from both CDI and DSC sample groups did not show the nitrogen peak (FIG. 8). Since HEMA chains do not have any nitrogen, appearance of the nitrogen peak confirms the formation of an amide bond between the primary amine ($—NH_2$) on the NA molecules and the hydroxyl groups (—OH) on the HEMA polymer chains. Since all the samples were subjected to ultrasonication post-NA conjugation, presence of any adsorbed NA was ruled out.

Understanding the Mode of Action of NA+pHEMA Surfaces

Figure 9B:
FIG. 9 shows hemocyte viability assay results. A: A representative image from a viability assay of hemocytes on NA-conjugated HEMA substrates treated with anti-noradrenaline antibody. Hemocytes exhibit Calcein-AM labeling and are negative for DAPI staining indicating cells are viable. B: A representative image from hemocytes adhering to NA+pHEMA substrates without anti-noradrenaline antibody. Hemocytes fail to label for Calcein-AM and are positive for DAPI labeling indicating that the cells are not viable and have compromised cells membranes. C: Hemocytes adhering to NA-HEMA substrates treated with anti-NA antibody labeled with phalloidin. Hemocytes display diffused pattern of actin filaments and an absence of stress filaments. D: Hemocytes adhering to NA+pHEMA substrates without anti-NA antibody treatment. Hemocytes adhering to NA+pHEMA surfaces displayed stressed actin filaments and an abnormal punctate distribution of actin. Inset box shows disintegrating enucleated hemocytes with signs of apoptotic blebbing.
Figure 9D:
Figure 9A:
Figure 9C:

Hemocytes adhering to NA+pHEMA polymer substrates treated with anti-NA antibody displayed Calcein-AM staining and lack of DAPI staining (FIG. 9A), indicating that hemocytes were viable with intact cell membranes. Hemocytes adhering to NA+pHEMA substrates without the anti-NA antibody labeled negative for Calcein-AM while labeling positive for DAPI (FIG. 9B), indicating that the cells were not viable and had a compromised cell membrane. Hemocytes adhering to NA+pHEMA substrates treated with anti-NA antibody did not show a stressed cytoskeleton as demonstrated by the cytoskeletal assay (FIG. 9C). Hemocytes adhering to NA+pHEMA substrates showed stressed F-actin filaments, membrane disintegration and blebbing (FIG. 9D and inset). For control surfaces the results were similar to samples treated with anti-NA antibody. The control substrates did not have any effect on the viability of cells and did not adversely affect the cytoskeleton of the cells, similar to results shown in FIGS. 9A and 9C.

Example 4

Effect of Noradrenaline on the Settling Behavior of Barnacle

Exploration of surfaces by invertebrate larvae is an important step leading to attachment and metamorphosis into juveniles. Oyster pediveliger larvae and barnacle cyprid larvae investigate surfaces using exploratory structures bearing an array of sensory cells. The effect of the neurotransmitter noradrenaline (NA) was investigated on the cyprids of the barnacle *Balanus amphitrite*. 1 day old cyprids were challenged with micro-molar concentrations of NA ranging from 30-100 mM and assayed over 5 days. Multidimensional imaging was carried out with Zeiss discovery V12 and Nikon AZ100 stereoscopes and samples were preserved for SEM analysis at 24 hour intervals. 'Searching behavior' of the cyprids was lost after NA challenge and they failed to cement to the substratum. A considerable delay in cyprid-adult ecdysis was noted. Remnants of cyprid organs such as the antennules were clearly visible in metamorphosed juveniles. Juvenile barnacles appeared to be normal when compared to the controls. Cyprids are compared to oyster larvae to understand the effects of NA on the signal transduction cascades involved in larval settlement and to explore NAs potential as a natural fouling deterrent.

Materials and Methods

One day old cypris larvae of the *B. amphitrite* were challenged with 30-µm range of noradrenaline. Cyprids were challenged in two different ways. One group was flash challenged for 3 hours then washed with artificial sea water (ASW) and incubated in ASW free of NA for the remaining duration of the experiment. The second group was incubated with NA for 24 hours then washed and incubated in ASW for the remaining duration of the experiment. Barnacle cyprids were monitored and assayed over period of 120 hours (5 days).

Cyprid metamorphosis was imaged at 24, 48, 96, 120 hour intervals. Images were taken at each intervals and samples preserved for SEM analysis. The cyprid larvae were imaged using, Zeiss discovery V12 stereo-microscope, Nikon AZ100 stereo-macroscope and the Hitachi-4800 field emission scanning electron microscope.

On the last day of the experiments the metamorphosed barnacles were assayed for viability. Viability was ascertained by observing the movement of cirri and ability of the metamorphosed barnacles to feed normally.

The experiments were repeated 4 times with 3 replicates per experiment.

Conclusions

NA inhibits the 'searching behavior' of the cyprid larvae. NA treated cyprids do not settle or cement to a substratum. NA treatment is not toxic to cyprid larvae. NA treatment considerably delays the cyprid-adult ecdysis. Remnants of cyprid organs are identifiable on the ecdysing barnacles. The effects of NA from 30-100 µM concentrations are similar with little variation. NA exerts similar effects on flash challenged as well as prolonged exposed cyprids. NA stimulation affects barnacle cyprids in the same exact manner as it affects oyster pediveliger larvae, indicating a high degree of conservation of receptors for catecholamines in *Phylums Mollusca* (oysters) and *Phylum Arthropoda* (barnacles).

Given the similar effects that NA exerts on both oyster and barnacle larvae, the repertoire of receptors mediating these effects appear to be similar in these two species. The ability of NA to prevent settling behavior yet allowing normal development offers an opportunity to intercede in the signal transduction involved in settling independent of the signal transduction involved in development. The pediveliger larvae of additional bivalve families, for example, Pectimidae (*Placopecten magellanicus*) and the Mytilidae (*Mytilus edulis*) bear catecholamine containing cells in the larval foot. These sensory cells are used in sensing surface cues during settlement. Because they may bear receptors for NA, they are targets for the present biofouling deterrence methods and compositions.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

Burgess, J. G., K. G. Boyd, et al. (2003). "The Development of a Marine Natural Product-based Antifouling Paint." *Biofouling* 19(1 supp 1): 197-205.

Clare, A. S., (1995) "Chemical signals in barnacles: old problems, new approaches, in New Frontiers in barnacle evolution." F. R. Schram and J. T. Hoeg, Editors. A. A. Balkema Publishers, Rotterdam.

Coon, S. L., D. B. Bonar, et al. (1986). "Chemical production of cultchless oyster spat using epinephrine and norepinephrine." *Aquaculture* 58: 255-262.

Coon, S. L., W. K., Fitt, and D. B. Bonar, (1990) "Competence and delay of metamorphosis in the Pacific oyster *Crassostrea gigas.*" *Marine Biology.* 106(3): p. 379-387.

Crisp, D. J., (1974) "Factors influencing the settlement of marine invertebrate larvae in chemoreception in marine organisms." P. T. Grant and A. M. Mackie, Editors, Academic Press: New York, p. 177.

Croll, R. P., D. L. Jackson, and E. E. Voronezhskaya, (1997) "Catecholamine-Containing Cells in Larval and Postlarval Bivalve Molluscs." *Biol Bull.* 193(2): p. 116-124.

Dahms, H.-U., T. Jin, et al. (2004). "Adrenoceptor Compounds Prevent the Settlement of Marine Invertebrate Larvae: *Balanus Amphitrite* (Cirripedia), *Bugula neritina* (Bryozoa) and *Hydroides elegans* (Polychaeta)." *Biofouling* 20(6): 313-321.

de Boer, B., H. K. Simon, et al. (2000). ""Living" free radical photopolymerization initiated from surface-grafted iniferter monolayers." *Macromolecules* 33(2): 349-356.

Hadfield, M. G., (1998) Research on settlement and metamorphosis of marine invertebrate larvae:past, present and future, The D. P. Wilson lecture. *Biofouling* 12(9).

Harris, B. P. and A. T. Metters (2006). "Generation and characterization of photopolymerized polymer brush gradients." *Macromolecules* 39(8): 2764-2772.

Hisashi Yamamoto, K. S. A. T. N. F., (1999) "Roles of dopamine and serotonin in larval attachment of the barnacle, *Balanus amphitrite.*" *Journal of Experimental Zoology* 284(7): p. 746-758.

Isoai, A., et al., (1996) "Molecular cloning of a new member of the putative G protein-coupled receptor gene from barnacle *Balanus amphitrite.*" *Gene.* 175(1-2): p. 95-100.

Lacoste, A., A. Cueff, et al. (2002). "P35-sensitive caspases, MAP kinases and Rho modulate b-adrenergic induction of apoptosis in mollusk immune cells" *Journal of Cell Science* 115: 761-768.

Lefkowitz, R. J., J.-P. Sun, et al. (2008). "A crystal clear view of the β-adrenergic receptor." *Nat Biotech* 26(2): 189-191.

Masayuki Yamato, M. O. F. K. A. K. Y. S. T. O. (1999). "Signal transduction and cytoskeletal reorganization are required for cell detachment from cell culture surfaces grafted with a temperature-responsive polymer." *Journal of Biomedical Materials Research* 44(1): 44-52.

Pawlik, J. R., (1992) "Chemical ecology of the settlement of benthic marine invertebrates." *Oceanography and Marine Biology.* An Annual Review 30: p. 273.

Rahane, S. B., S. M. Kilbey, et al. (2005). "Kinetics of surface-initiated photoiniferter-mediated photopolymerization." *Macromolecules* 38(20): 8202-8210.

Shin-Ichi Sawada, Y. I. N. N. K. I. (2006). "Stress response of adherent cells on a polymer blend surface composed of a segmented polyurethane and MPC copolymers." *Journal of Biomedical Materials Research Part A* 79A(3): 476-484.

Shunji Nagahara, T. M. (1996). "Cell-substrate and cell-cell interactions differently regulate cytoskeletal and extracellular matrix protein gene expression." *Journal of Biomedical Materials Research* 32(4): 677-686.

Walters, L. J., G. Miron, and E. Bourget, (1999) "Endoscopic observations of invertebrate larval substratum exploration and settlement." Marine ecology progress series, 182: p. 95.

Yebra, D. M., S. Kiil, et al. (2004). "Antifouling technology—past, present and future steps towards efficient and environmentally friendly antifouling coatings." *Progress in Organic Coatings* 50(2): 75-104.

Zimmer-Faust, R. K., M. N. Tamburri, and A. W. Decho, (1996) "Chemosensory ecology of oyster larvae: benthic-pelagic coupling, in Zooplankton: Sensory ecology and physiology." P. H. Lenz, et al., Editors, Gordon and Breach: Amsterdam. p. 37.

Throughout this application, various publications are referenced. The disclosures of these publications in their entireties are hereby incorporated by reference into this application in order to more fully describe the state of the art to which this invention pertains.

What is claimed is:

1. An anti-fouling surface comprising noradrenaline conjugated to a polymer, the polymer including a vinyl resin, a vinyl ester, a vinyl chloride, a polymer of methacrylic acid, or a polymer of 2-hydroxyethyl methacrylate; wherein,
the polymer is grafted to the surface and the polymer attaches the noradrenaline to the surface, the surface being a marine or aquatic surface that contacts fresh water, brackish water, or salt water during use, the anti-fouling surface being resistant to settling and cementation of marine life on the surface.

2. The anti-fouling surface of claim 1, wherein the anti-fouling surface is resistant to settling and cementation of mollusks, crustaceans, Bryozoa, and/or polychaet.

3. The anti-fouling surface of claim 2, wherein the anti-fouling surface is resistant to settling and cementation of oysters.

4. The anti-fouling surface of claim 2, wherein the anti-fouling surface is resistant to settling and cementation of barnacles.

5. The anti-fouling surface of claim 1, wherein the polymer is a component of a marine paint or varnish.

6. The anti-fouling surface of claim 1, wherein the surface is at least a portion of the hull of a ship, a propeller, a seismic streamer, a dock, an oil rig, a gas rig, a pipeline, a power plant water intake system, a heat exchanger, a grid, a fish net, or a cage.

7. The anti-fouling surface of claim 1, wherein the surface comprises metal, wood, concrete or plastic.

8. The anti-fouling surface of claim 1, wherein the surface is a metal surface.

9. An anti-fouling surface comprising noradrenaline conjugated to a polymer, the polymer comprising —COOH or —OH side groups, the noradrenaline being conjugated to the polymer via reaction between the noradrenaline and the —COOH or —OH side groups; wherein,
the polymer is grafted to the surface and the polymer attaches the noradrenaline to the surface, the surface being a marine or aquatic surface that contacts fresh water, brackish water, or salt water during use, the anti-fouling surface being resistant to settling and cementation of marine life on the surface.

10. The anti-fouling surface of claim 9, wherein the anti-fouling surface is resistant to settling and cementation of mollusks, crustaceans, Bryozoa, and/or polychaet.

11. The anti-fouling surface of claim 10, wherein the anti-fouling surface is resistant to settling and cementation of oysters.

12. The anti-fouling surface of claim 10, wherein the anti-fouling surface is resistant to settling and cementation of barnacles.

13. The anti-fouling surface of claim 9, wherein the polymer is a component of a marine paint or varnish.

14. The anti-fouling surface of claim 9, wherein the surface is at least a portion of the hull of a ship, a propeller, a seismic streamer, a dock, an oil rig, a gas rig, a pipeline, a power plant water intake system, a heat exchanger, a grid, a fish net, or a cage.

15. The anti-fouling surface of claim 9, wherein the surface comprises metal, wood, concrete or plastic.

16. The anti-fouling surface of claim 9, wherein the surface is a metal surface.

17. The anti-fouling surface of claim 9, wherein the surface further comprises a phenolic resin, a silicone polymer, a chlorinated rubber, a coal tar, an epoxy resin, a polyamide resin, a vinyl resin, an elastomer, an acrylate polymer, a fluoropolymer, a polyester, a polyurethane, or a latex.

18. The anti-fouling surface of claim 9, wherein the polymer is a polymer of methacrylic acid, or a polymer of 2-hydroxyethyl methacrylate.

* * * * *